United States Patent
Miyazawa et al.

(10) Patent No.: US 6,348,244 B1
(45) Date of Patent: *Feb. 19, 2002

(54) LIQUID-CRYSTAL COMPOUNDS HAVING LARGE NEGATIVE VALUE OF PERMITTIVITY ANISOTROPY, LIQUID-CRYSTAL COMPOSITION, AND LIQUID-CRYSTAL DISPLAY ELEMENT

(75) Inventors: Kazutoshi Miyazawa; Hiroyuki Takeuchi; Yasuhiro Kubo; Fusayuki Takeshita; Etsuo Nakagawa, all of Chiba (JP)

(73) Assignee: Chisso Corporation, Osaka (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/529,989
(22) PCT Filed: Oct. 26, 1998
(86) PCT No.: PCT/JP98/04834
  § 371 Date: Apr. 24, 2000
  § 102(e) Date: Apr. 24, 2000
(87) PCT Pub. No.: WO99/21816
  PCT Pub. Date: May 6, 1999

(30) Foreign Application Priority Data
  Oct. 24, 1997 (JP) .............................................. 9-309918

(51) Int. Cl.[7] ........................ C09K 19/34; C09K 19/30; C09K 19/42; C07C 25/18; C07C 309/06; C07C 319/06
(52) U.S. Cl. .............. 428/1.1; 252/299.61; 252/299.63; 252/299.66; 549/356; 549/369; 570/127; 570/129; 570/131
(58) Field of Search ...................... 252/299.63, 299.61, 252/299.66, 299.01; 570/127, 129, 131; 549/369, 356; 428/1.1

(56) References Cited

U.S. PATENT DOCUMENTS 5,670,085 A * 9/1997 Miyazawa et al. ...... 252/299.01

FOREIGN PATENT DOCUMENTS

| DE | 3839213 A1 * | 5/1990 |
| GB | 2249309 | 5/1992 |
| JP | 6-228037 | 8/1994 |

OTHER PUBLICATIONS

CAPLUS 1991: 33205.*
Matharu, A.S. et al., "The synthesis and comparison of the liquid crystalline properties of certain 1–(4'–n–alkoxy–polyfluorobiphenyl–4–yl)–2–(trans–4–n–pentylcyclohexyl)–ethenes and–ethanes carrying four, six or eight fluoro–substituents", Liq. Cryst., vol. 23, No. 4, (1997) pp. 575–588.

Byron, D.J. et al., "The synthesis and liquid crystal properties of certain 1–(4'–n–alkoxy–2,2',3,3',5,5',6,6'–octafluorobiphenyl–4–yl)–2(trans–4–n–pentylcyclohexyl) ethanes and –ethenes", Liq. Cryst., vol. 19, No. 1 (1995) pp. 39–45.

Gray, et al., "The Synthesis and Transition Temperatures of Some 4,4"–Dialkyl–and 4,4"–Alkoxyalkyl–1,1':4'1Δ–terphenyls with 2,3–or2',3'–Difluoro Substitutents and of their Biphenyl Analogues", J. Chem. Soc. Perkin Trans. 11, 1989, 2041–2053.

Hird, et al., "The Synthesis and Transition Temperatures of Some Ortho–Dichloroterphenyls For Ferroelectric Mixtures", Mol. Cryst. Liq. Cryst. 1995, vol. 260, pp. 227–240.

Reiffenrath, et al., "New Liquid–crystalline compounds with negative dielectric anisotrophy", Liquid Crystals, 1989, vol. 5, No. 1, 159–170.

* cited by examiner

Primary Examiner—Shean C. Wu
(74) Attorney, Agent, or Firm—Wenderoth, Lind & Ponack, L.L.P.

(57) ABSTRACT

An object of the present invention is to provide novel liquid crystalline compounds having a negative and extremely large dielectric anisotropy value and a small optical anisotropy value together, to provide liquid crystal compositions comprising the liquid crystalline compound, and to provide liquid crystal display devices fabricated by using the liquid crystal composition; the liquid crystalline compounds have 2,3-difluorophenyl moiety and are expressed by the general formula (1)

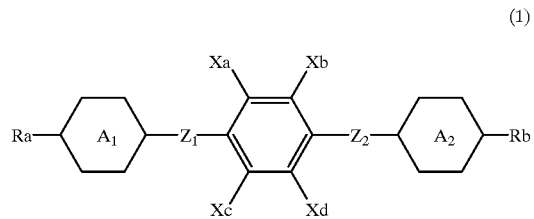

(1)

wherein Ra and Rb each independently represent a straight chain or branched alkyl group having 1 to 10 carbon atoms in which group any methylene group may be replaced by —O—, —CH=CH—, or —C≡C—, but there is not a case wherein —O— continues; ring $A_1$ represents cyclohexane-1,4-diyl not adjacent any methylene group may be replaced by —O—; ring $A_2$ represents 2,3-difluoro-1,4-phenylene in which phenylene hydrogen atoms at 5-position and 6-position may each independently be replaced by fluorine atoms; $Z_1$ and $Z_2$ each independently represent single bond or —$CH_2CH_2$—; Xa, Xb, Xc, and Xd each independently represent hydrogen atom, fluorine atom, or chlorine atom, but at least one of Xa, Xb, Xc, and Xd is fluorine atom or chlorine atom and any atom which constitutes the compound may be replaced by its isotope.

19 Claims, No Drawings

LIQUID-CRYSTAL COMPOUNDS HAVING LARGE NEGATIVE VALUE OF PERMITTIVITY ANISOTROPY, LIQUID-CRYSTAL COMPOSITION, AND LIQUID-CRYSTAL DISPLAY ELEMENT

This application is a 371 application of PCT/JP98/04834 filed Oct. 26, 1998.

TECHNICAL FIELD

The present invention relates to novel liquid crystalline compounds and liquid crystal compositions. More specifically, the invention relates to liquid crystalline compounds having 2,3-difluorophenyl moiety, liquid crystal compositions comprising the compound, and liquid crystal display devices fabricated by using the liquid crystal composition.

BACKGROUND ART

Liquid crystal display devices fabricated by using liquid crystalline compounds (the term "liquid crystalline compounds" is used in this specification as a generic name for the compounds which exhibit a liquid crystal phase and the compounds which do not exhibit a liquid crystal phase but are useful as a component of liquid crystal compositions) are widely being used for the display of computers, television sets, and the likes.

For the purpose of reducing the power consumption and decreasing the leakage of electromagnetic wave, liquid crystal compositions are required to lower their driving voltage. Driving voltage (threshold voltage) is known to be a function of dielectric anisotropy value and elastic constant according to the following equation (M. F. Leslie, Mol. Cryst. Liq. Cryst., 12, 57 (1970)):

$$Vth=\pi(K/\epsilon_0\Delta\epsilon)^{1/2}$$

wherein Vth represents a threshold voltage, $\epsilon_0$: a dielectric constant in vacuum, K: an elastic constant, and $\Delta\epsilon$: a dielectric anisotropy, respectively.

That is, it can be understood that in order to lower driving voltage, it is necessary 1) to increase dielectric anisotropy value or 2) to decrease elastic constant.

It is generally considered to be difficult to adjust the value of the elastic constant of liquid crystalline compounds, and thus a means in which the dielectric anisotropy value is increased is principally adopted to lower the driving voltage. Accordingly, novel liquid crystalline compounds having a large dielectric anisotropy value are long-expected.

From some time ago, a characteristic of narrow visual angle is considered to be a most serious problem to liquid crystal display devices, and various display modes have been proposed in recent years for the purpose of improving the narrow visual angle. In-plane switching (IPS) display devices proposed in 1995 greatly widened the visual angle compared with conventional display devices (Liquid Crystal Conference in Japan 2A07 (1995), ASIA DISPLAY '95, 557 (1995) and ASIA DISPLAY '95, 707 (1995)).

Also, in 1997, an attempt was reported in which a vertical alignment (VA) cell was used (SID 97 DIGEST, 845 (1997)), and the display devices of this mode are considerably wide in visual angle compared with conventional display devices.

In either mode of IPS and VA, characteristics required of liquid crystal compositions are 1) a negative and large dielectric anisotropy value ($\Delta\epsilon$) for lowering driving voltage, and 2) a small optical anisotropy value ($\Delta n$) for keeping $\Delta n \cdot d$ (product of optical anisotropy value multiplied by cell thickness) at an optimum value.

However, compounds having simultaneously a negative and large dielectric anisotropy value and a small optical anisotropy value are heretofere unknown, and thus novel liquid crystalline compounds having such characteristics have been long-expected.

As compounds having a negative and large dielectric anisotropy value and a comparatively small optical anisotropy value, the compound of the following formula (13) is known (V. Reifffenrath et al., Liq. Cryst., 5 (1), 159 (1989)). It is reported that the dielectric anisotropy value of this compound is ($\Delta\epsilon=-4.1$) and optical anisotropy value is ($\Delta n=0.18$).

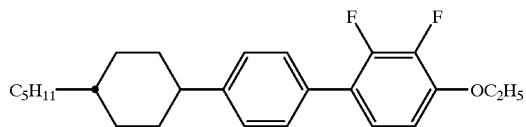

(13)

However, the dielectric anisotropy value of the compound can not be said to be sufficiently large, and a satisfactory lowering of driving voltage was unable to actualize.

As compounds having a negative dielectric anisotropy value, the terphenyl compound of the formula (14) is known (J. Chem. Soc. Perkin Trans. II 2, 2041 (1989)). This compound is narrow (10.5° C.) in the temperature range showing nematic phase and exhibits smectic phase in a wide temperature range (50.5° C.). Further, terphenyl compounds were extremely large in optical anisotropy value in general and were unsuitable as component of liquid crystal compositions for IPS mode or VA mode.

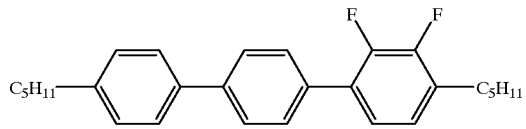

(14)

The phenomenon that dielectric anisotropy value is increased in negative when fluorine atom is introduced at a lateral position of a phenylene group which constitutes the skeleton of liquid crystalline compounds is well known to a person skilled in the art. On the other hand, the order parameters of liquid crystalline compounds are decreased by the introduction of fluorine atom to the lateral position. Dielectric anisotropy value and optical anisotropy value are regarded as functions of the order parameters (W. Maier and G. Meier, Z. Naturf. (a), 16 262 (1961)), and the decrease of the order parameters caused by the introduction of fluorine atom will bring about the decrease in dielectric anisotropy value. Accordingly, the introduction of fluorine atom to the lateral position does not necessarily produce a large increase in negative dielectric anisotropy value (Theory of Maier and Meier).

DISCLOSURE OF THE INVENTION

In view of the several characteristics described above and required of liquid crystal compositions, an object of the present invention is to provide liquid crystalline compounds having a negative and extremely large dielectric anisotropy value and a small optical anisotropy value at the same time, to provide liquid crystal compositions comprising the compound, and to provide liquid crystal display devices fabricated by using the liquid crystal composition.

As a result of diligent research and development conducted by the present inventors to solve the problems described above, it has been found that the liquid crystalline compounds expressed by the general formula (1) have desired characteristics, leading to the accomplishment of the present invention.

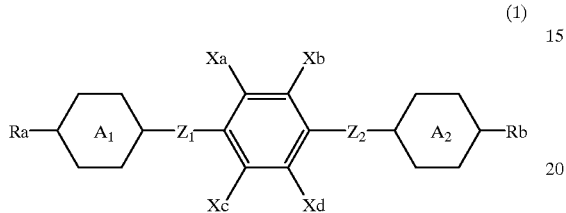
(1)

wherein Ra and Rb each independently represent a straight chain or branched alkyl group or alkoxy group having 1 to 10 carbon atoms, or a straight chain or branched alkenyl group or alkynyl group having 2 to 10 carbon atoms; ring $A_1$ represents cyclohexane-1,4-diyl in which ring not-adjacent any methylene group may be replaced by —O—; ring $A_2$ represents 2,3-difluoro-1,4-phenylene in which phenylene hydrogen atoms at 5-position and 6-position may each independently be replaced by fluorine atoms, but there is not a case wherein both of the hydrogen atoms are simultaneously replaced; $Z_1$ and $Z_2$ each independently represent single bond or —CH$_2$CH$_2$—; Xa, Xb, Xc, and Xd each independently represent hydrogen atom, fluorine atom, or chlorine atom, but at least one of Xa, Xb, Xc, and Xd is fluorine atom or chlorine atom; and any atom which constitutes the compound may be replaced by its isotope.

Among the liquid crystalline compounds expressed by the general formula (1), the compounds which exhibit particularly preferable characteristics are those expressed by one of the following general formulas (1-1) to (1-18)

(1-1)
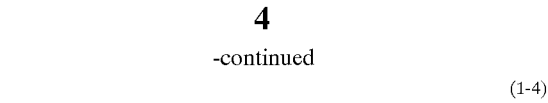

(1-2)
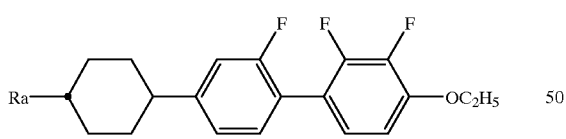

(1-3)
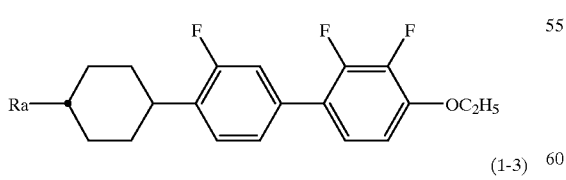

-continued (1-4)
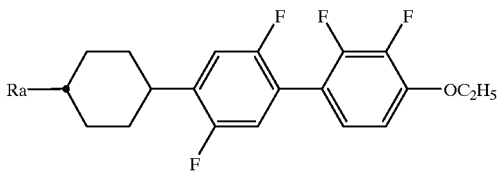

(1-5)
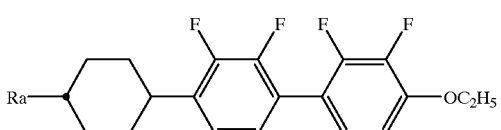

(1-6)
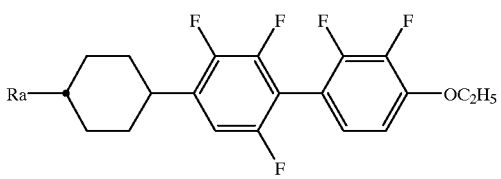

(1-7)
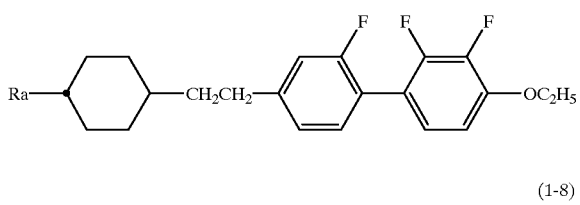

(1-8)
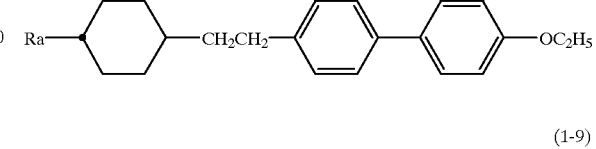

(1-9)
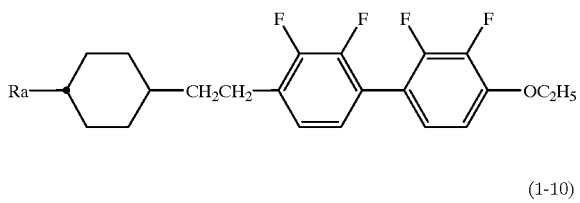

(1-10)
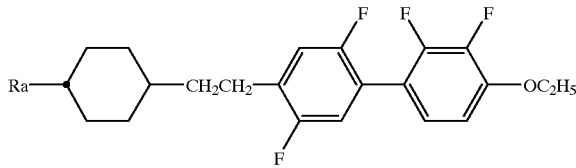

(1-11)
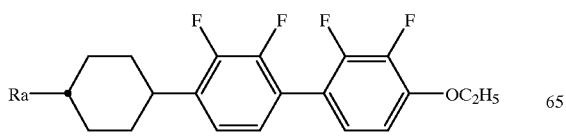

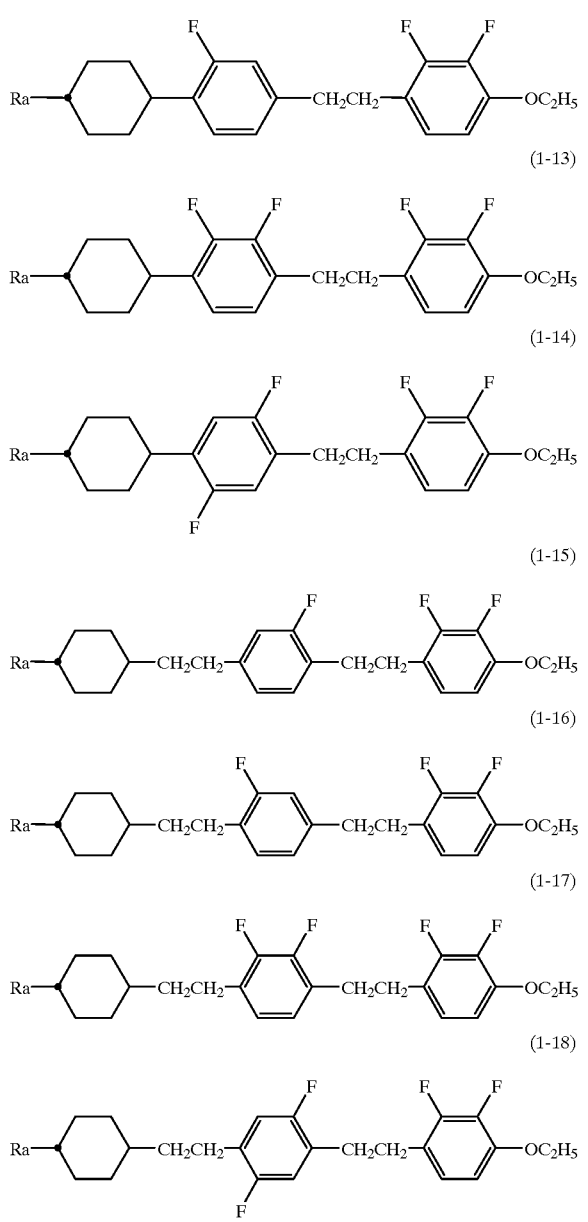

In the general formula (1), Ra and Rb are alkyl groups, alkoxy groups, alkoxyalkyl groups, alkoxyalkoxy groups, alkenyl groups, or alkynyl groups. Compounds in which Ra and Rb are alkyl groups, alkoxy groups, alkoxyalkyl groups, or alkoxyalkoxy groups are chemically stable, and the compounds in which Ra and Rb are alkenyl groups or alkynyl groups exhibit a slightly large optical anisotropy.

Also, the compounds in which Ra and Rb are alkyl groups, alkoxy groups, or alkenyl groups are preferable since they have a low viscosity. Further, when used for display devices of IPS mode or VA mode, the compounds in which Ra and Rb are alkyl groups or alkoxy groups are optimum since a high chemical stability and a small optical anisotropy value are required in such case.

While $Z_1$ and $Z_2$ are each independently single bond or —$CH_2CH_2$—, the compounds in which one of $Z_1$ and $Z_2$ is single bond have a lower viscosity and the compounds in which one of them is —$CH_2CH_2$— have nematic phase in a wider temperature range. Group —$CH_2CH_2$— is preferably introduced to $Z_1$, and when it is introduced to $Z_2$, compounds are provided of which the upper limit of the temperature range exhibiting nematic phase is slightly low.

While Xa, Xb, Xc, and Xd are each independently hydrogen atom, fluorine atom, or chlorine atom, at least one of Xa, Xb, Xc, and Xd is a halogen atom. In the halogen atoms, fluorine atom is preferable, and when it is chlorine atom, compounds having a slightly high viscosity are provided.

Number of the halogen atom is preferably 1, 2, or 3, and 1 or 2 is desirable to obtain compounds having a low viscosity.

While ring $A_1$ is cyclohexane-1,4-diyl, 1,3-dioxane-2,5-diyl, or tetrahydropyran-2,5-diyl, cyclohexane-1,4-diyl is optimum to obtain compounds having a low viscosity. Compounds in which 1,3-dioxane-2,5-diyl is introduced to the position of ring $A_1$ have a small elastic constant value (K), and are preferable since they lower the driving voltage of liquid crystal display devices of TN mode including IPS mode or VA mode.

Further, any atom which constitutes the compounds of the present invention may be replaced by its isotope since the compounds in which the atom is replaced by the isotope exhibit the same characteristics.

Compounds of the present invention expressed by the general formula (1) can be produced by using known procedures of organic synthetic chemistry in a suitable combination. The known procedures of organic chemistry can be found by consulting such books as organic Synthesis, Organic Reactions, and Shin-Jikken Kagaku Kouza (Course of New Chemical Experiment), and their typical examples are shown below.

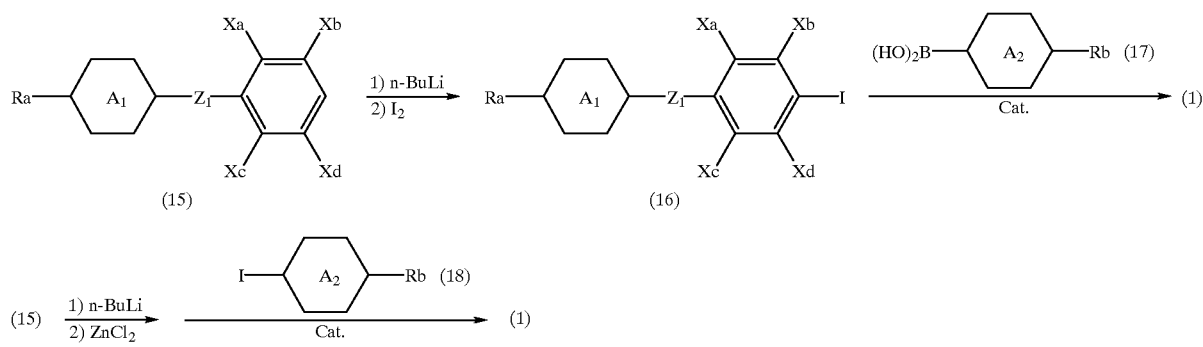

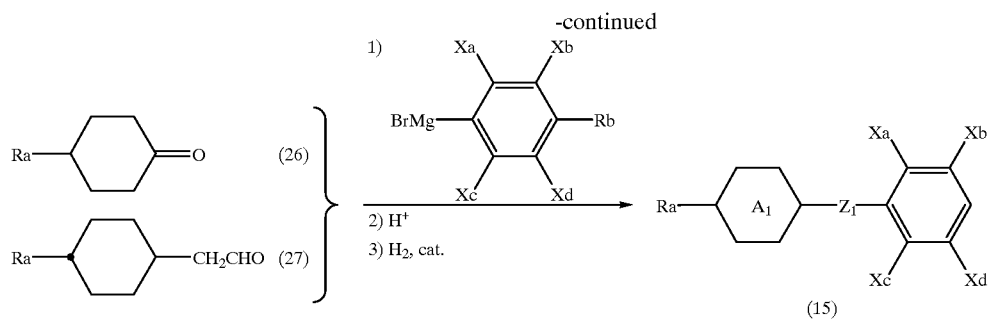

Compounds expressed by the general formula (1) wherein $Z_2$ is single bond can be produced, for instance, by the following method. That is, iodized benzene derivative (16) can be obtained by reacting halogenated benzene derivative (15) with n- or sec-butyl lithium and then reacting with iodine. Increase of yield can be expected by selecting the type of butyl lithium to be used depending on the position and number of halogen atom in halogenated benzene derivative (15).

Compounds of the general formula (1) can be produced by reacting the iodized benzene derivative (16) with phenyl boric acid derivative (17) in the presence of a catalyst to perform a cross-coupling reaction. While the catalyst to be used is preferably Pd or Ni type, any catalyst may be. used so far as it makes the reaction smoothly proceed. The phenyl boric acid derivative (17) can be produced by reacting a corresponding phenyl magnesium halide derivative with an boric acid ester at a low temperature.

Further, the compounds of the general formula (1) can be produced by converting halogenated benzene derivative (15) into an organic zinc compound and then reacting with phenyl halide derivative (18) in the presence of a catalyst. While the catalyst to be used is preferably Pd or Ni type, any catalyst may be used so far as it makes the reaction smoothly proceed.

Halogenated benzene derivative (15) can be produced by reacting cyclohexanone derivative (26) or aldehyde deriva-tive (27) with a Grignard reagent (28) and then subjecting to a dehydration reaction and hydrogenation reaction in the same manner as described above.

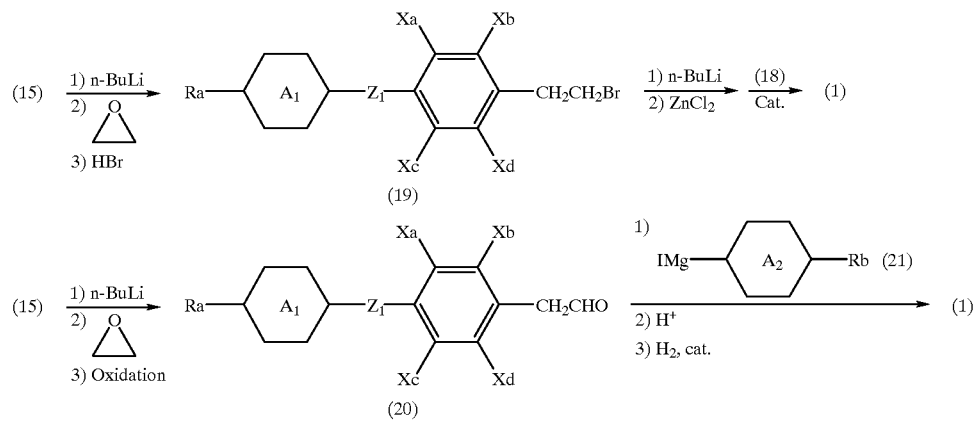

Compounds expressed by the general formula (1) wherein $Z_2$ is $-CH_2CH_2-$ can be produced by the method described below. That is, compound (19) can be produced by reacting the halogenated benzene derivative (15) described above with n- or sec-butyl lithium and then with ethylene oxide to obtain an alcohol derivative, and subsequently halogenating (preferably brominating or iodinating) the alcohol derivative. Compounds of the general formula (1) can be produced by reacting the compound (19) with metal lithium under ultrasonic radiation to convert into an organic lithium compound, reacting in-situ with zinc chloride to form a zinc compound, and then reacting it with the phenyl halide derivative (18) described above in the presence of a catalyst. While the catalyst to be used is preferably Pd or Ni type, a Pd catalyst of zero valent is particularly preferable.

Compounds of the general formula (1) can also be obtained by reacting halogenated benzene derivative (15) with n- or sec-butyl lithium and subsequently with ethylene oxide to obtain an alcohol derivative, oxidizing it to convert into aldehyde derivative (20), reacting it with a Grignard reagent (21) which can be prepared from phenyl halide derivative (18), and further subjecting it to a dehydration reaction and a hydrogenation reaction in turn.

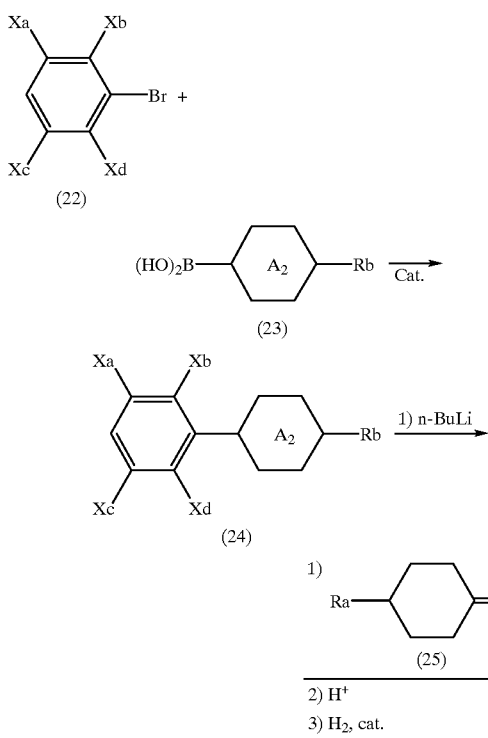

Compounds expressed by the general formula (1) wherein ring $A_1$ is cyclohexane-1,4-diyl can preferably be produced by the following method. That is, biphenyl derivative (24) can be produced by reacting halogenated phenyl bromide or halogenated phenyl iodide (22) with phenyl boric acid derivative (23) in the presence of a catalyst to perform a cross-coupling reaction. Compounds of the general formula (1) can be obtained by reacting biphenyl derivative (24) with n- or sec-butyl lithium and subsequently with cyclohexanone derivative (25), and then subjecting it to a dehydration reaction and hydrogenation reaction as in the case described above.

In order to introduce 1,3-dioxane-2,5-diyl or tetrahydropyran-2,5-diyl to the position of ring $A_1$, it is sufficient to follow the method disclosed by H. M. Vorbrodt, R. Eidenschink et al. (H. M. Vorbrodt, J. Prakt, Chem., 323, 902 (1981), R. Eidenschink, DE-OS3306960).

Since the liquid crystalline compounds of the present invention obtained by such a method exhibit a negative and extremely large dielectric anisotropy, low voltage driving of liquid crystal display devices can be actualized.

Also, since the liquid crystalline compounds of the present invention are sufficiently stable physically and chemically under conditions wherein liquid crystal display devices are ordinarily used, are readily mixed with various liquid crystal materials, and have an extremely excellent miscibility even at low temperatures, the compounds are remarkably excellent as component of nematic liquid crystal compositions.

These compounds have a negative and large dielectric anisotropy value and a comparatively small optical anisotropy value at the same time, and can preferably be used as component of liquid crystal compositions for IPS mode or VA mode in particular.

Liquid crystal compositions of the present invention are described below. Liquid crystal compositions of the present invention preferably comprise at least one compound expressed by the general formula (1) in the ratio of 0.1 to 99.9% by weight to develop excellent characteristics, and the amount is more desirably 1 to 60% by weight.

Still more desirably, the liquid crystal compositions of the present invention are completed by mixing a compound arbitrarily selected from the group consisting of the compounds expressed by one of the general formulas (2) to (12) depending on the purpose of the liquid crystal compositions, in addition to a first component comprising at least one compound expressed by the general formula (1).

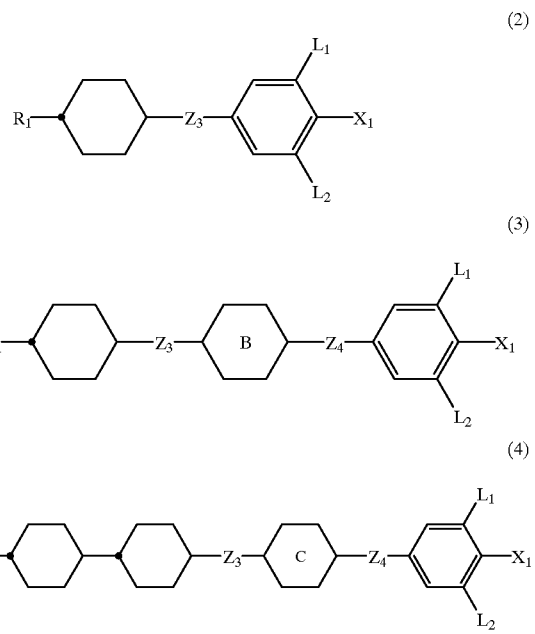

wherein $R_1$ represents an alkyl group having 1 to 10 carbon atoms in which group not-adjacent any methylene group may be replaced by —O— or —CH=CH— and any hydrogen atom in the group may be replaced by fluorine atom; $X_1$ represents fluorine atom, chlorine atom, —OCF$_3$, —OCF$_2$H, —CF$_3$, —CF$_2$H, —CFH$_2$, —OCF$_2$CF$_2$H, or —OCF$_2$CFHCF$_3$; $L_1$ and $L_2$ each independently represent hydrogen atom or fluorine atom; $Z_3$ and $Z_4$ each independently represent —CH$_2$CH$_2$—, —(CH$_2$)$_4$13 , —COO—, —CF$_2$O—, —OCF$_2$—, —CH=CH—, or single bond; ring B represents cyclohexane-1,4-diyl or 1,3-dioxane-2,5-diyl, or 1,4-phenylehe in which hydrogen atom may be replaced by fluorine atom; ring C represents cyclohexane-1,4-diyl, or 1,4-phenylene in which hydrogen atom may be replaced by fluorine atom; and any atom which constitutes these compounds may be replaced by its isotope,

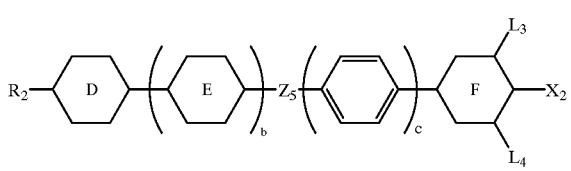

(6)

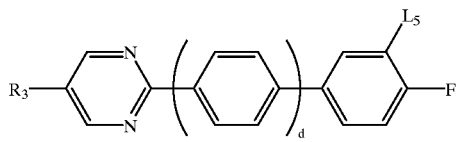

(11)

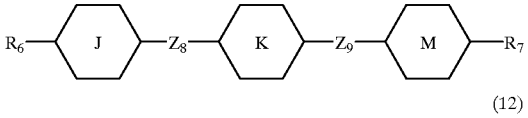

(12)

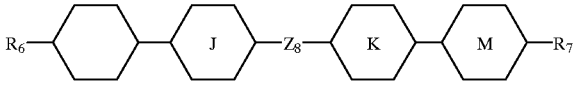

wherein $R_2$ and $R_3$ each independently represent an alkyl group having 1 to 10 carbon atoms in which group not-adjacent any methylene group may be replaced by —O— or —CH=CH— and any hydrogen atom in the group may be replaced by fluorine atom; $X_2$ represents —CN or —C—≡C—CN; ring D represents cyclohexane-1,4-diyl, 1,4-phenylene, 1,3-dioxane-2,5-diyl, or pyrimidine-2,5-diyl; ring E represents cyclohexane-1,4-diyl, 1,4-phenylene in which hydrogen atom may be replaced by fluorine atom, or pyrimidine-2,5-diyl; ring F represents cyclohexane-1,4-diyl or 1,4-phenylene; $Z_5$ represents —CH$_2$CH$_2$—, —COO—, or single bond; $L_3$, $L_4$, and $L_5$ each independently represent hydrogen atom or fluorine atom; b, c, and d are each independently 0 or 1; and any atom which constitutes these compounds may be replaced by its isotope, wherein $R_6$ and $R_7$ each independently represent an alkyl group having 1 to 10 carbon atoms in which group not-adjacent any methylene group may be replaced by —O— or —CH=CH— and any hydrogen atom in the group may be replaced by fluorine atom; ring J, ring K, and ring M each independently represent cyclohexane-1,4-diyl or pyrimidine-2,5-diyl, or 1,4-phenylene in which hydrogen atom may be replaced by fluorine atom; $Z_8$ and $Z_9$ each independently represent —CH$_2$CH$_2$—, —C≡C—, —COO—, —CH=CH—, or single bond; and any atom which constitutes these compounds may be replaced by its isotope.

Compounds expressed by one of the general formulas (2) to (9) are a second component, and the compounds expressed by one of the general formulas (10) to (12) are a third component in the liquid crystal compositions of the present invention, respectively.

As preferable examples of the compounds used in the liquid crystal compositions of the present invention and expressed by one of the general formulas (2) to (4), the compounds of the following general formulas can be mentioned:

(7)

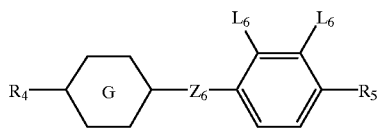

(8)

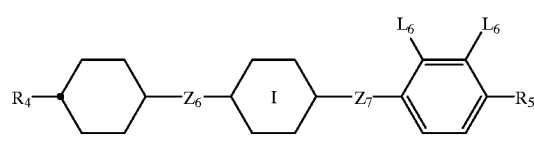

(9)

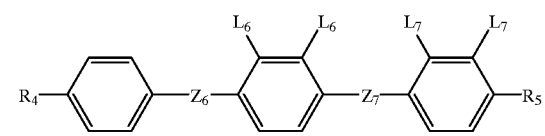

wherein $R_4$ and $R_5$ each independently represent an alkyl group having 1 to 10 carbon atoms in which group not-adjacent any methylene group may be replaced by —O— or —CH=CH— and any hydrogen atom in the group may be replaced by fluorine atom; ring G and ring I each independently represent cyclohexane-1,4-diyl or 1,4-phenylene; $L_6$ and $L_7$ each independently represent hydrogen atom, cyano group, or fluorine atom, but there is not a case wherein $L_6$ and $L_7$ represent hydrogen atom at the same time; $Z_6$ and $Z_7$ each independently represent —CH$_2$CH$_2$—, —COO—, or single bond; and any atom which constitutes these compounds may be replaced by its isotope, (10)

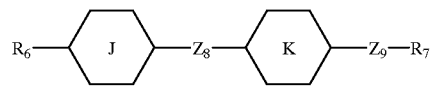

(2-1)

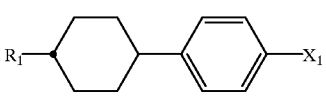

(2-2)

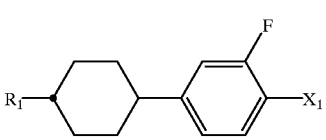

(2-3)

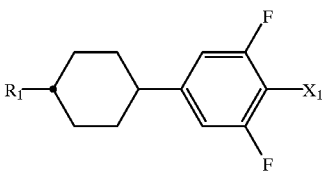

(2-4)

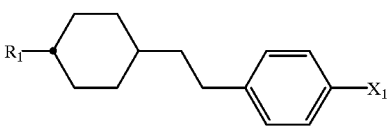

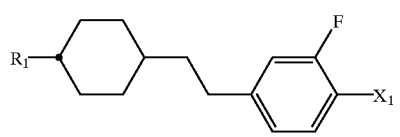
(2-5)
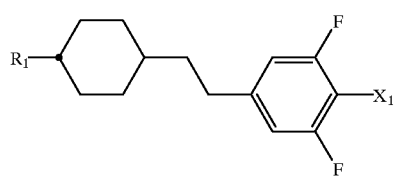
(2-6)
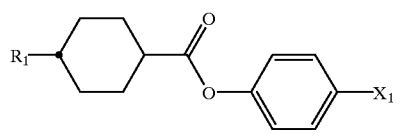
(2-7)
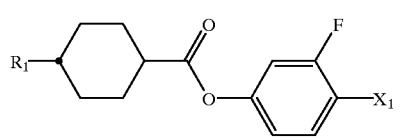
(2-8)
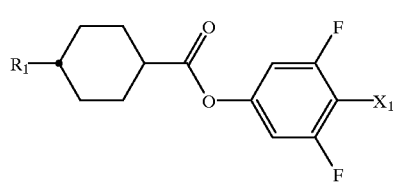
(2-9)
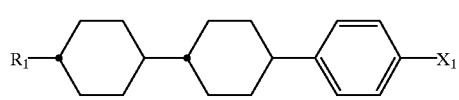
(3-1)
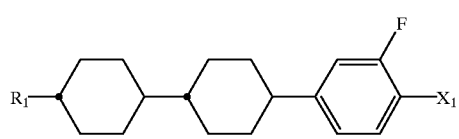
(3-2)
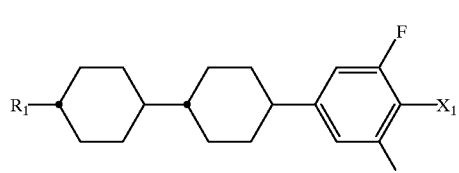
(3-3)
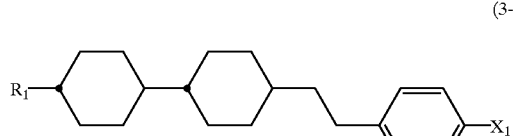
(3-4)
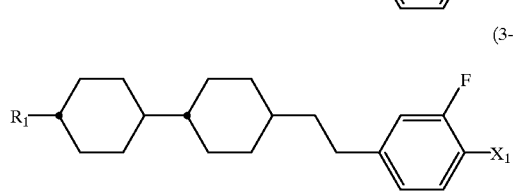
(3-5)
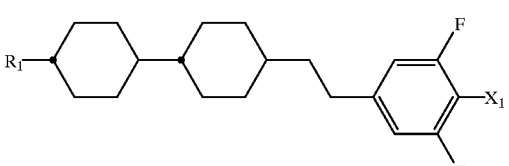
(3-6)
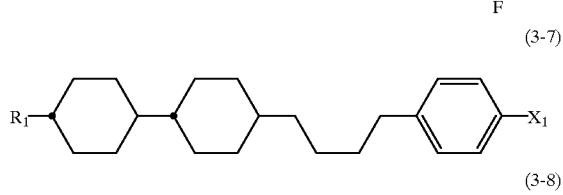
(3-7)
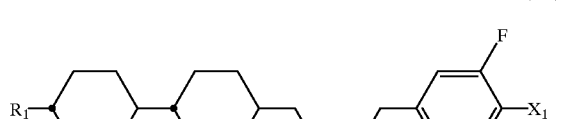
(3-8)
(3-9)
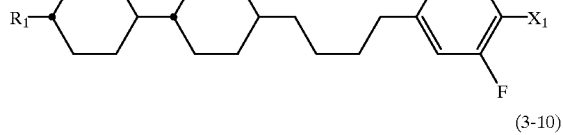
(3-10)
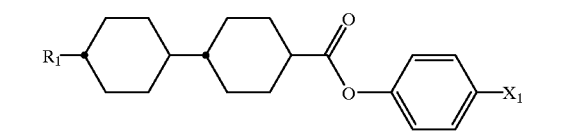
(3-11)
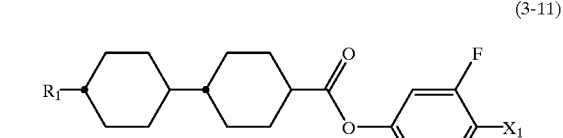
(3-12)
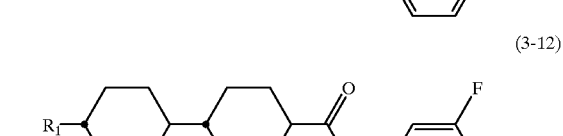
(3-13)
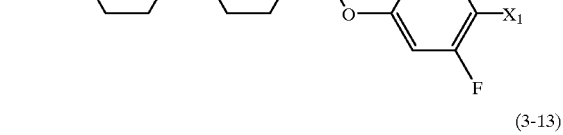
(3-14)
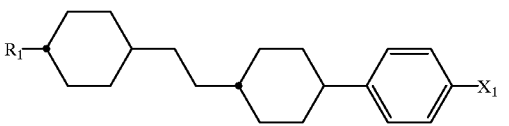
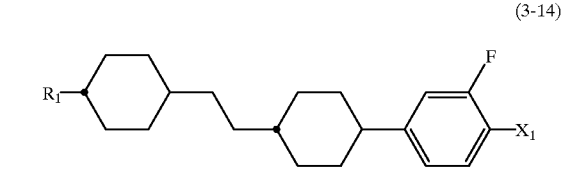

(3-15) 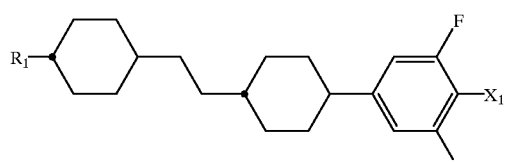
(3-16) 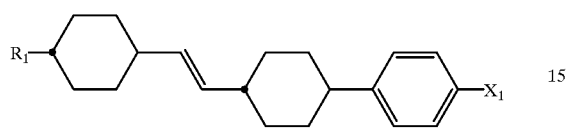
(3-17) 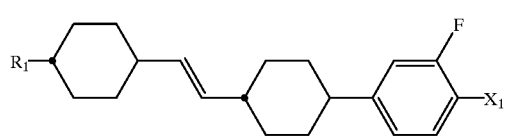
(3-18) 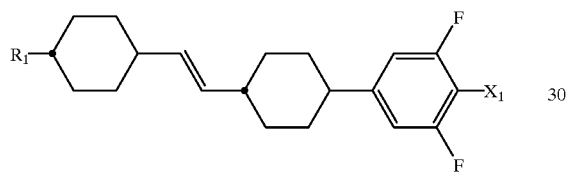
(3-19) 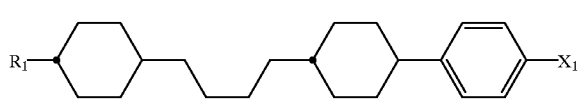
(3-20) 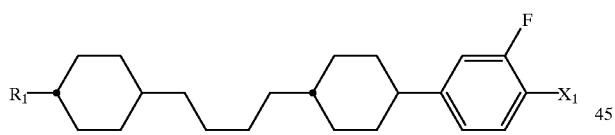
(3-21) 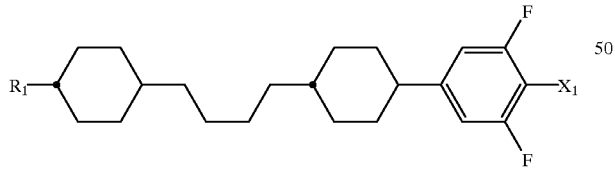
(3-22) 
(3-23) 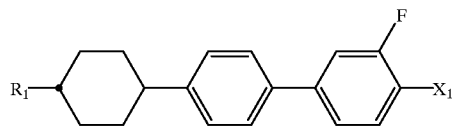
(3-24) 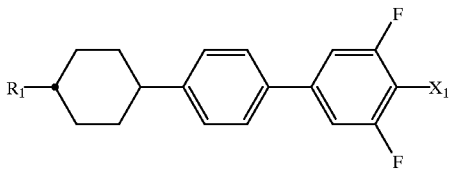
(3-25) 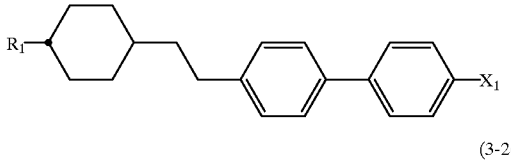
(3-26) 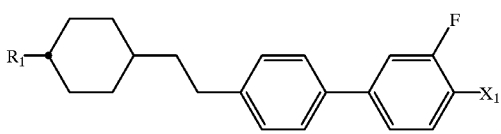
(3-27) 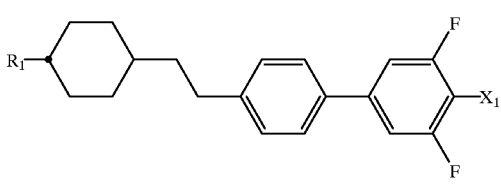
(3-28) 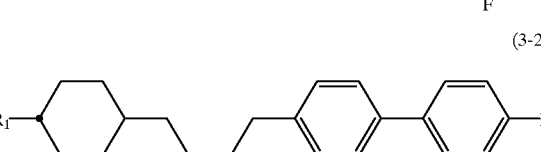
(3-29) 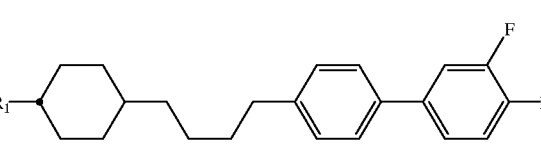
(3-30) 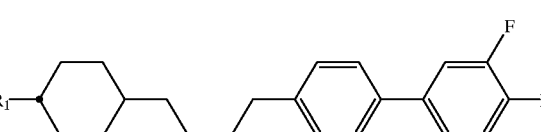
(3-31) 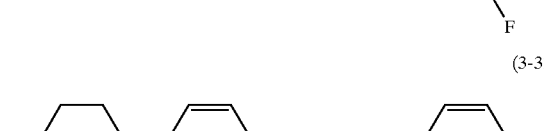
(3-32) 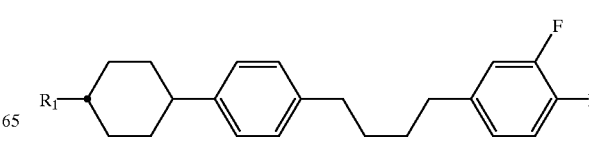

(3-33)
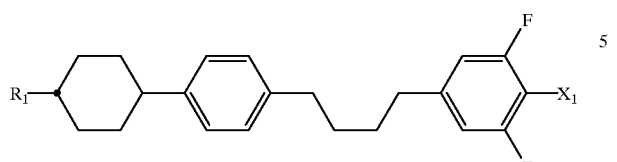
(3-34)
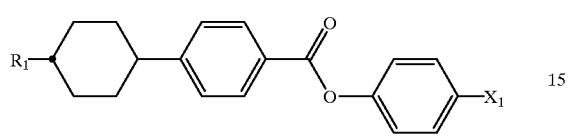
(3-35)
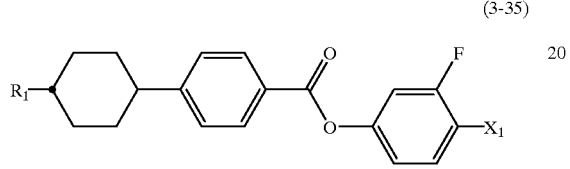
(3-36)
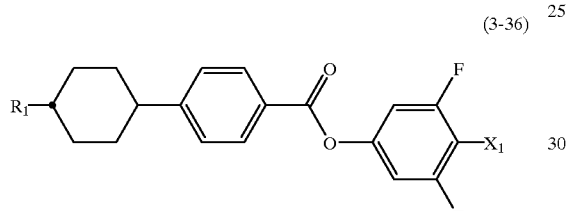
(3-37)
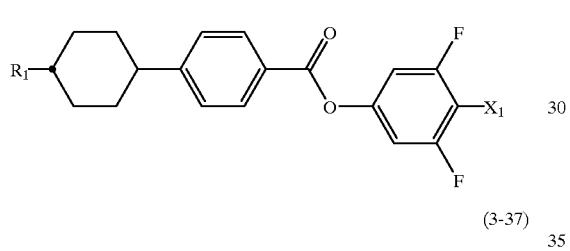
(3-38)
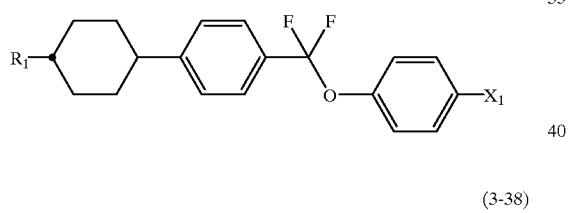
(3-39)
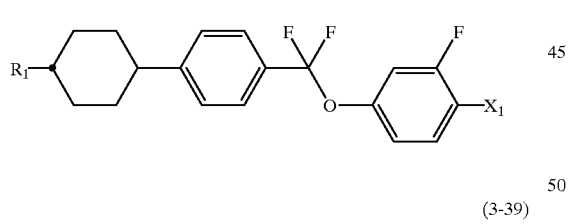
(3-40)
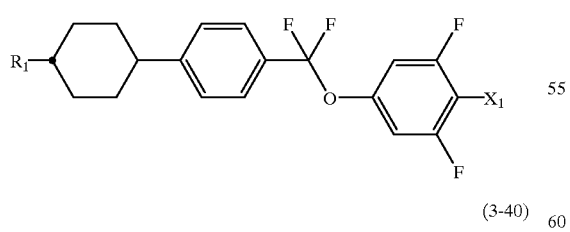
(3-41)
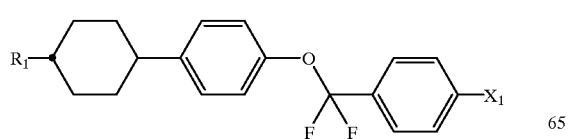
(3-42)
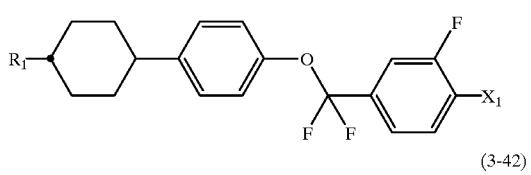
(3-43)
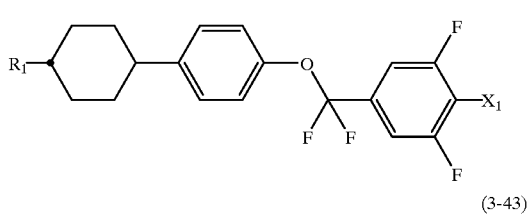
(3-44)
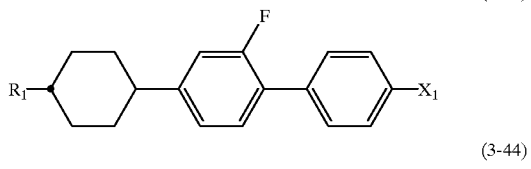
(3-45)
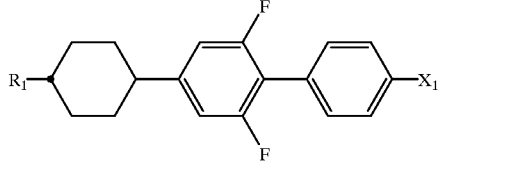
(3-46)
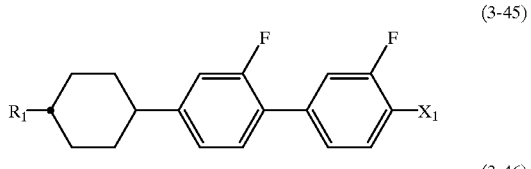
(3-47)
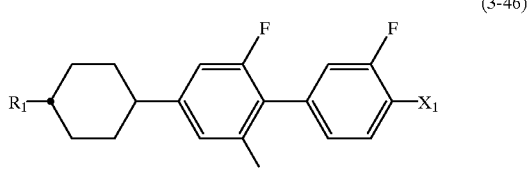
(3-48)
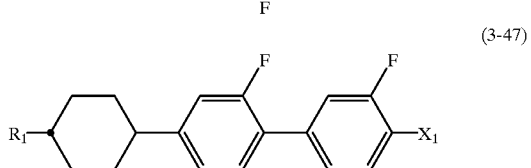
(3-49)
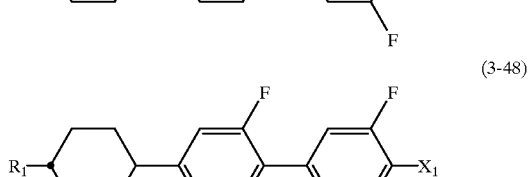

(3-50)
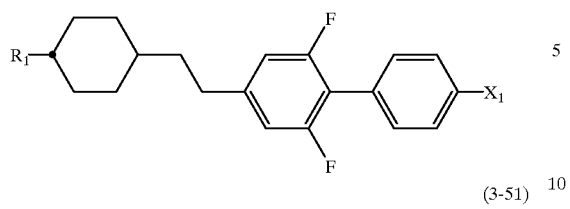
(3-51)
(3-52)
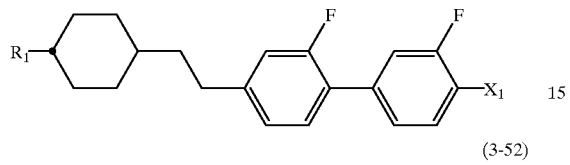
(3-53)
(3-54)
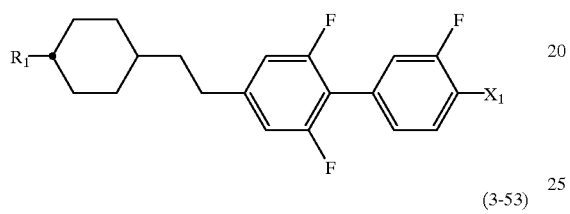
(3-55)
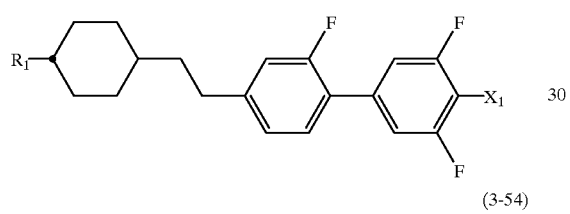
(3-56)
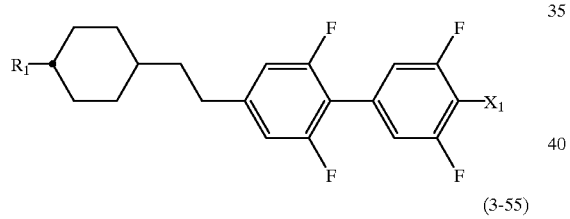
(3-57)
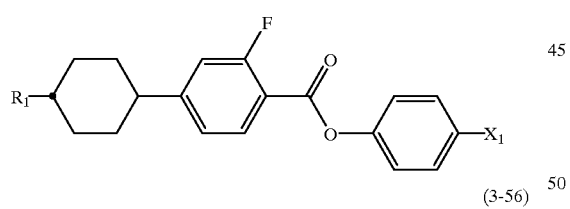
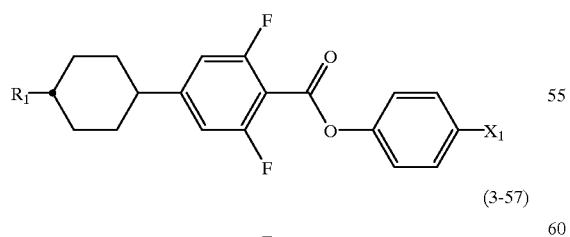
(3-58)
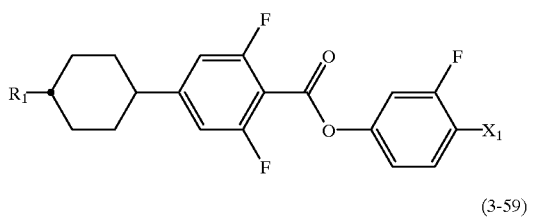
(3-59)
(3-60)
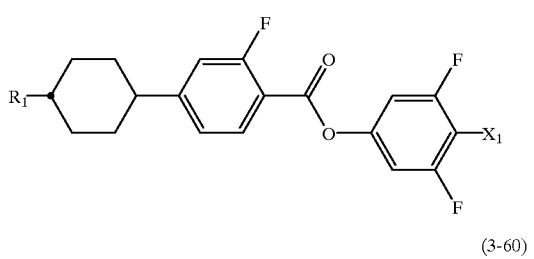
(3-61)
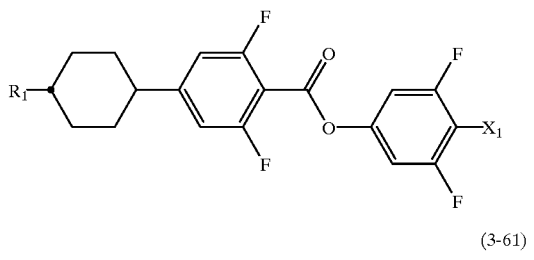
(3-62)
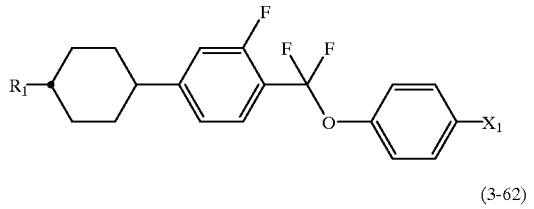
(3-63)
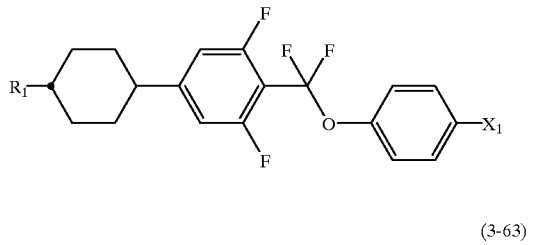
(3-64)
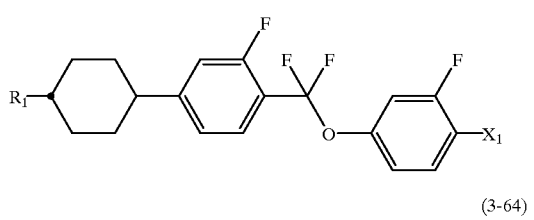
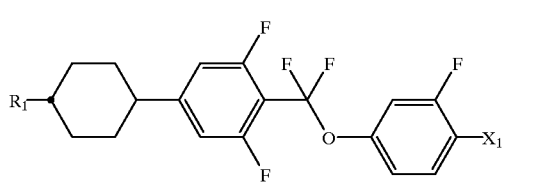

(3-65)
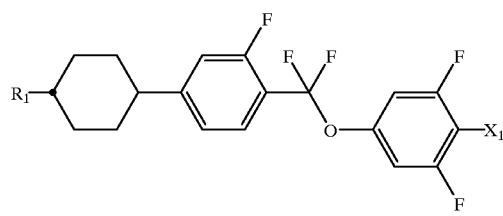
(3-66)
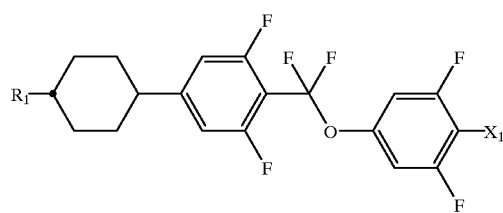
(3-67)
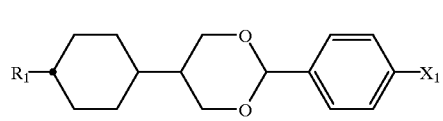
(3-68)
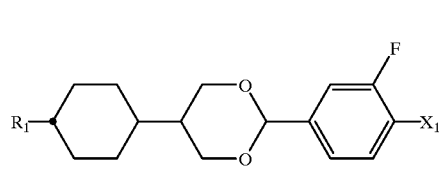
(3-69)
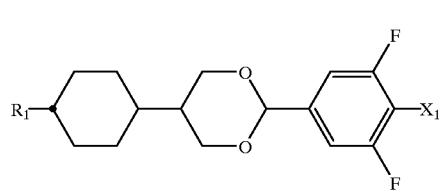
(4-1)
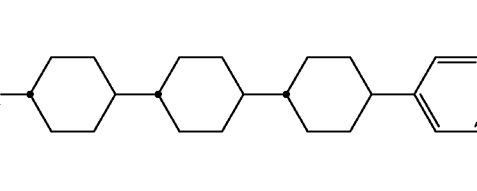
(4-2)
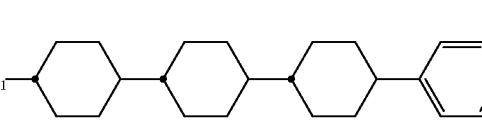
(4-3)
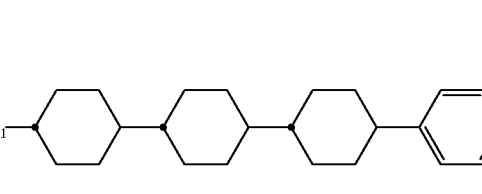
(4-4)
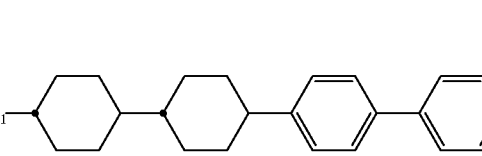
(4-5)
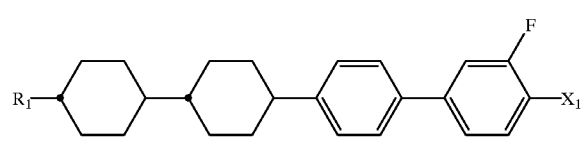
(4-6)
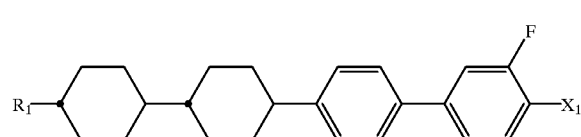
(4-7)
(4-8)
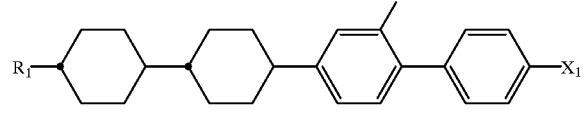
(4-9)
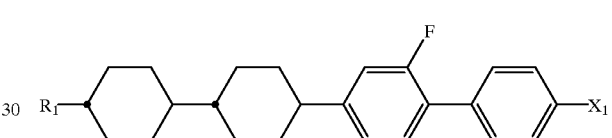
(4-10)
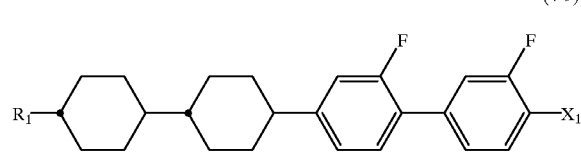
(4-11)
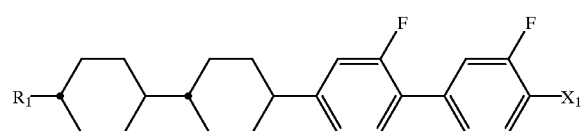
(4-12)
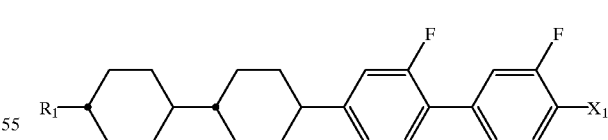

(4-13) 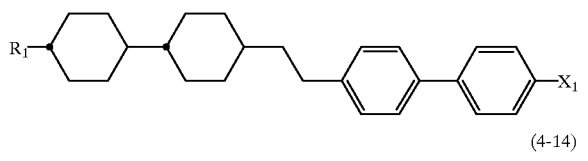

(4-14) 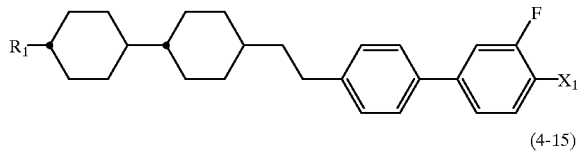

(4-15) 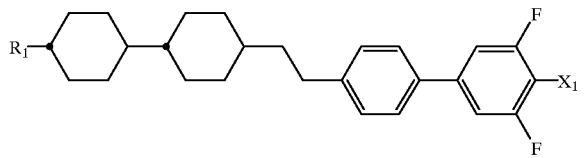

(4-16) 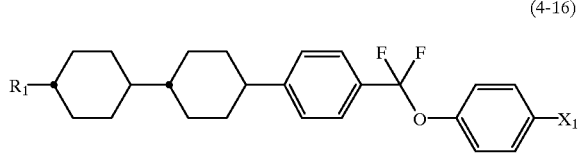

(4-17) 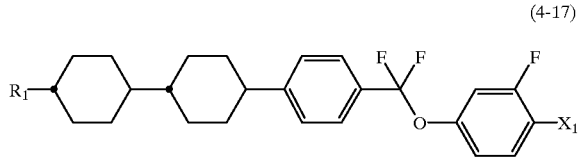

(4-18) 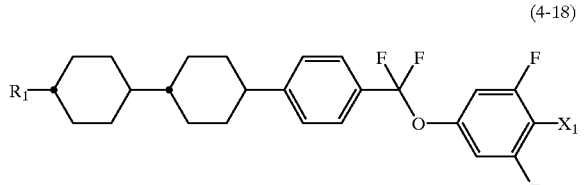

(4-19) 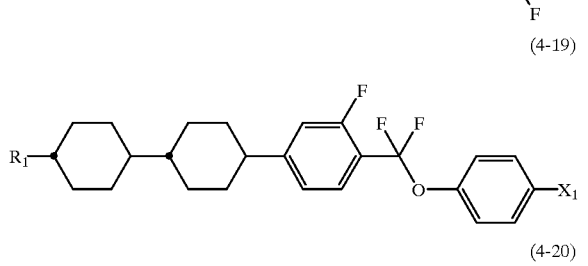

(4-20) 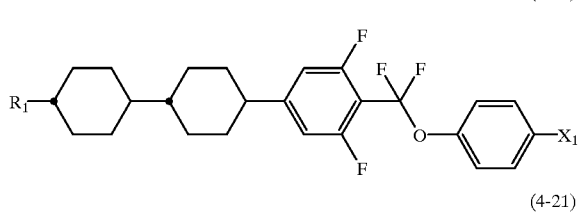

(4-21) 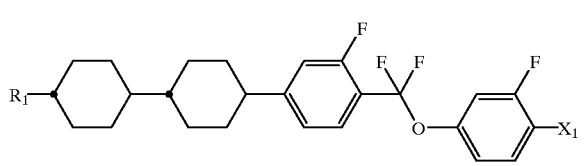

(4-22) 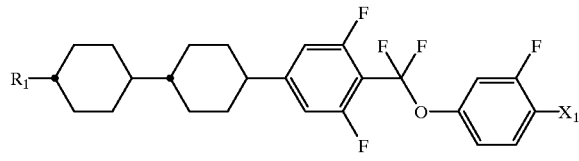

(4-23) 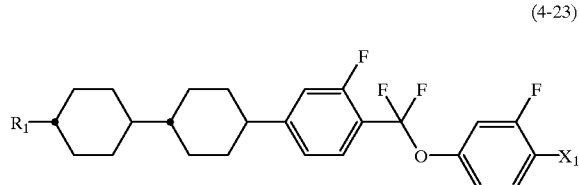

(4-24) 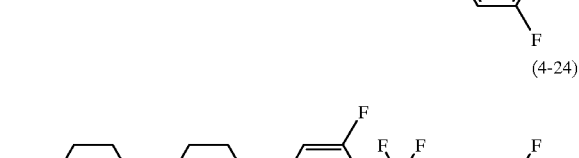

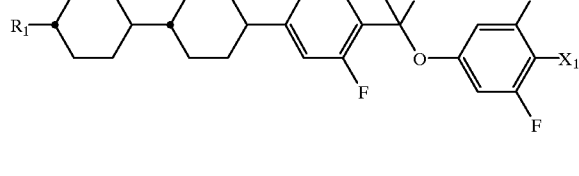

wherein $R_1$ and X1 have the same meaning as described above.

Compounds expressed by one of the general formulas (2) to (4) have a positive dielectric anisotropy value, are remarkably excellent in thermal stability and chemical stability, and are extremely useful especially when liquid crystal compositions for AM (active matrix), particularly for TFT (thin film transistor) of which a high reliability such as a high voltage holding ratio and a large specific resistivity is required are produced.

When liquid crystal compositions for AM are produced, the compound expressed by one of the general formulas (2) to (4) can be used in the range of 0.1 to 99.9% by weight based on the total amount of liquid crystal composition, the amount is preferably 10 to 97% by weight and more desirably 40 to 95% by weight. Besides, the compound expressed by one of the general formulas (10) to (12) may further be added for the purpose of adjusting viscosity.

Even when liquid crystal compositions for STN or TN are produced, the compound expressed by one of the general formulas (2) to (4) can be used, but its amount is preferably less than 50% by weight.

As preferable examples of the compounds used in the liquid crystal compositions of the present invention and expressed by the general formula (5) or (6), the compounds of the following general formulas can be mentioned:

(5-1) 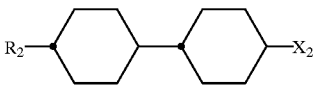

(5-2) 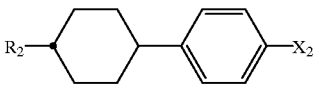

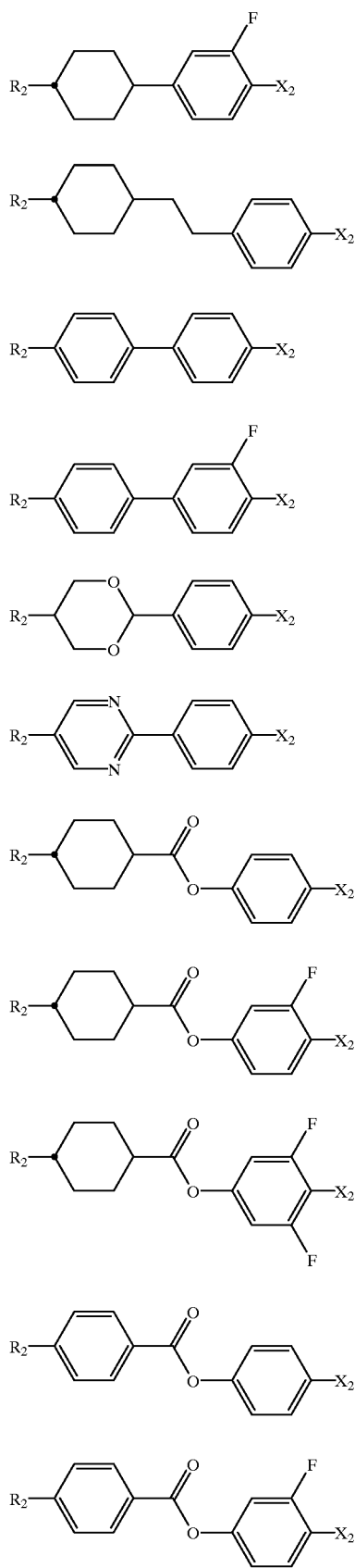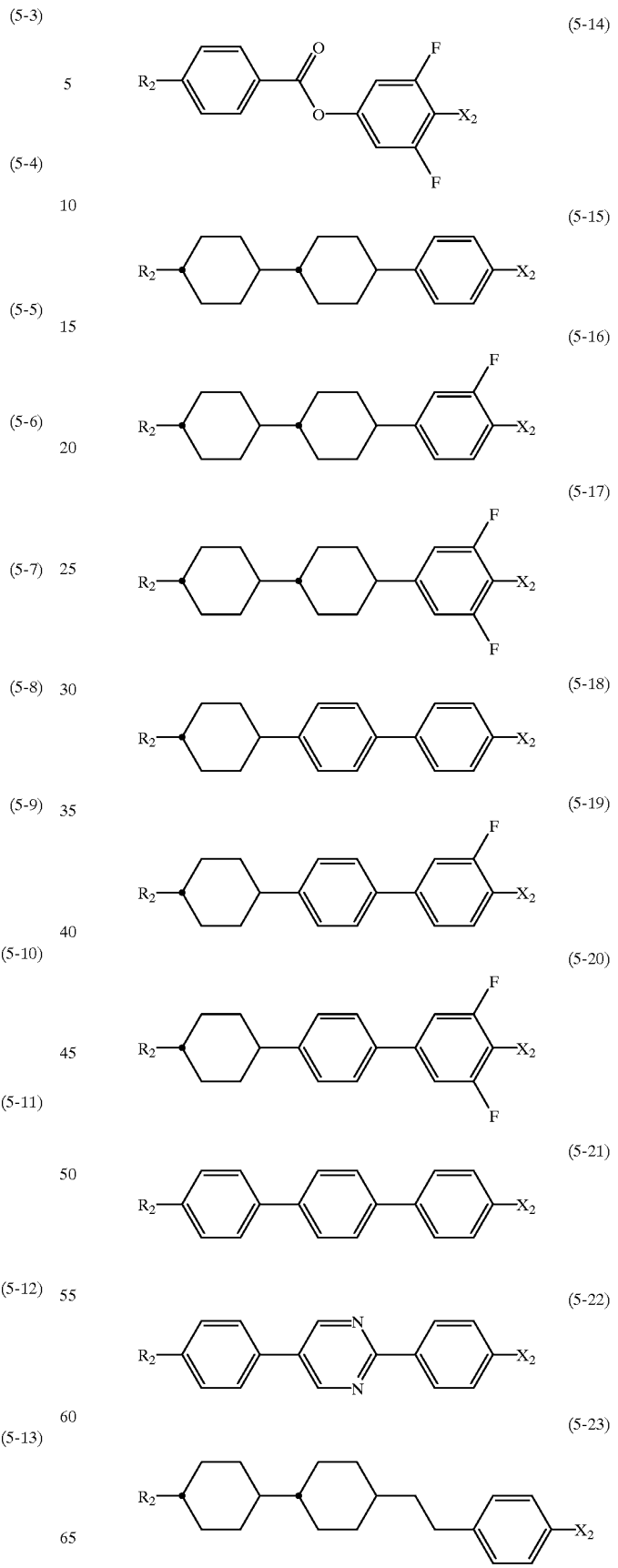

(5-24)
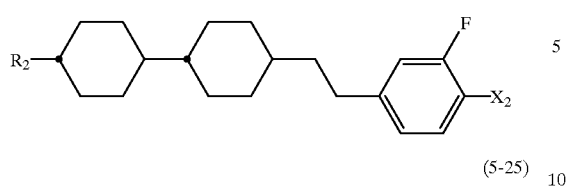
(5-25)
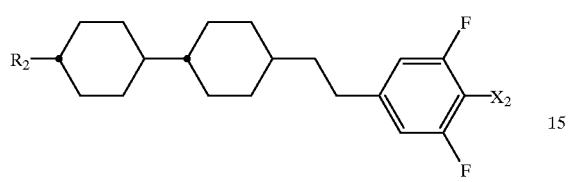
(5-26)
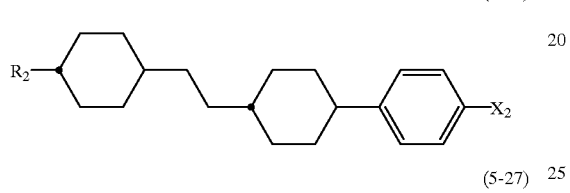
(5-27)
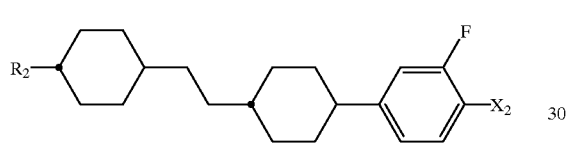
(5-28)
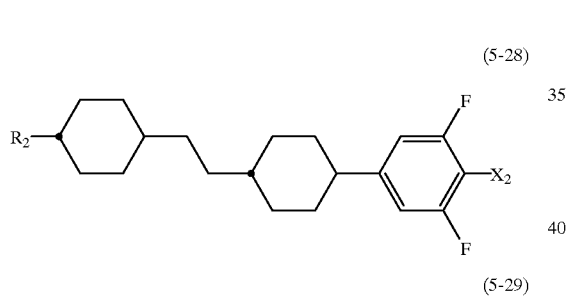
(5-29)
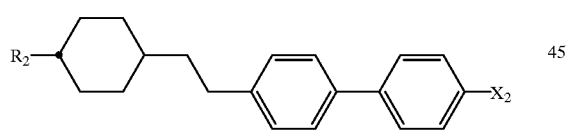
(5-30)
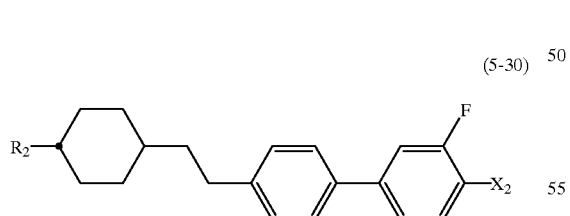
(5-31)
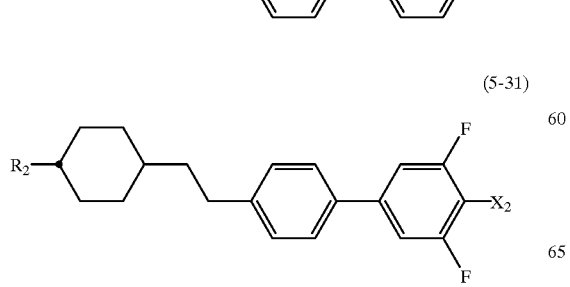
(5-32)
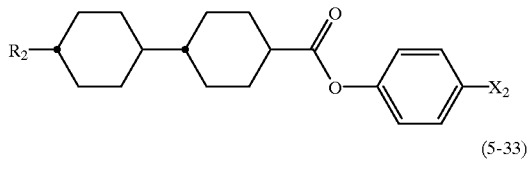
(5-33)
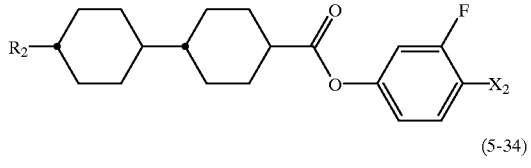
(5-34)
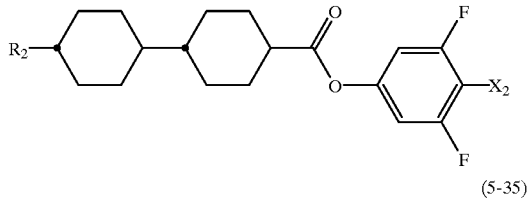
(5-35)
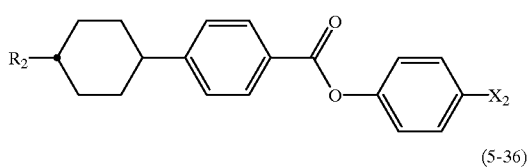
(5-36)
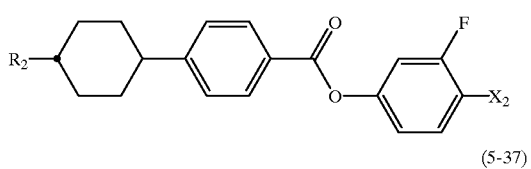
(5-37)
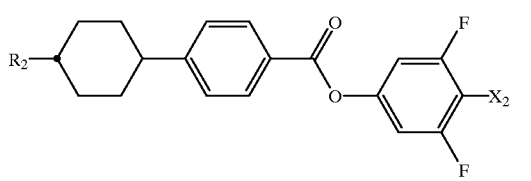
(5-38)
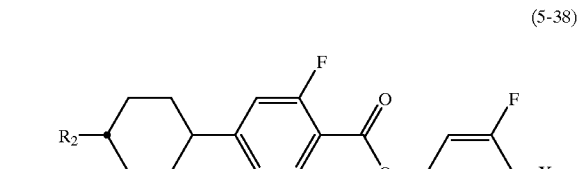
(5-39)
(5-40)
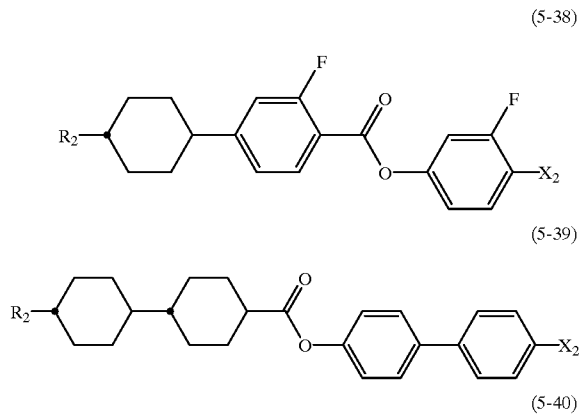

(6-1)
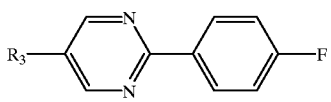

(6-2)
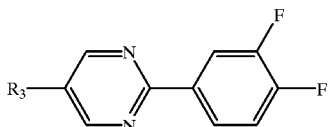

(6-3)
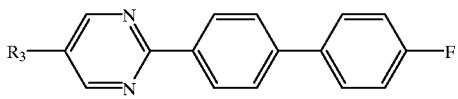

wherein $R_2$, $R_3$, and $X_2$ have the same meaning as described above.

Compounds expressed by the general formula (5) or (6) have a large positive dielectric anisotropy value, and are used particularly for the purpose of lowering threshold voltage of liquid crystal compositions. Also, they are used for the purpose of adjusting optical anisotropy value and widening nematic range such as raising clearing point. Further, they are used for the purpose of improving the steepness of voltage-transmittance curve of liquid crystal compositions for STN or TN.

Compounds expressed by the general formula (5) or (6) are particularly useful when liquid crystal compositions for STN or TN are produced.

When the amount of the compound expressed by the general formula (5) or (6) is increased in liquid crystal compositions, threshold voltage of liquid crystal compositions lowers but viscosity rises. Accordingly, it is advantageous to use a large amount of the compound since liquid crystal display devices can be driven at a low voltage so far as the viscosity of liquid crystal compositions satisfies a required value. When liquid crystal compositions for STN or TN are produced, the compound expressed by the general formula (5) or (6) can be used in the range of 0.1 to 99.9% by weight based on the total amount of liquid crystal composition, and the amount is preferably 10 to 97% by weight and more desirably 40 to 95% by weight.

As preferable examples of the compounds used in the liquid crystal compositions of the present invention and expressed by one of the general formulas (7) to (9), the compounds of the following general formulas can be mentioned:

(7-1)
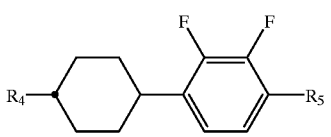

(7-2)
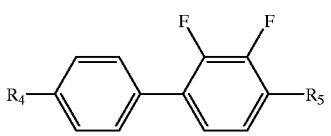

(7-3)
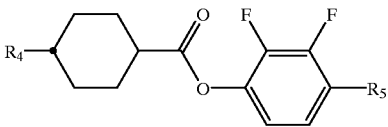

(8-1)
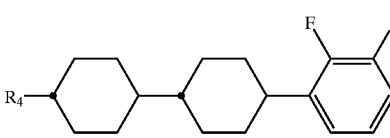

(8-2)
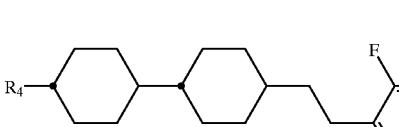

(8-3)
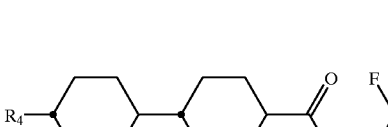

(8-4)

(8-5)
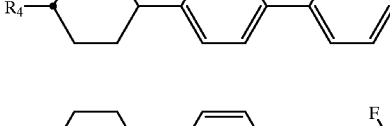

(9-1)
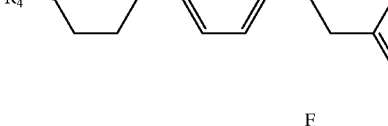

(9-2)
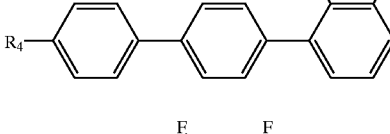

(9-3)
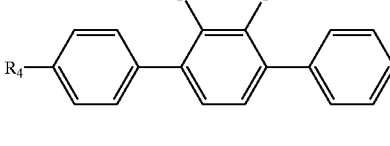

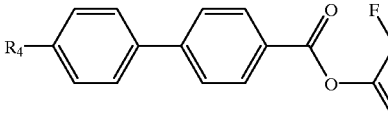

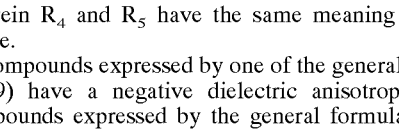

wherein $R_4$ and $R_5$ have the same meaning as described above.

Compounds expressed by one of the general formulas (7) to (9) have a negative dielectric anisotropy. Since the compounds expressed by the general formula (7) are two rings compounds, they are used principally for the purpose of adjusting threshold voltage, adjusting viscosity, or adjusting optical anisotropy value. Compounds expressed by the general formula (8) are used for the purpose of widening nematic range such as raising ;clearing point and for the purpose of adjusting optical anisotropy value. Compounds expressed by the general formula (9) are used for the purpose of adjusting optical anisotropy value.

Compounds expressed by one of the general formulas (7) to (9) are used principally for liquid crystal compositions having a negative dielectric anisotropy value. When the amount of the compound expressed by one of the general formulas (7) to (9) is increased in liquid crystal compositions, threshold voltage of liquid crystal compositions lowers but viscosity rises. Accordingly, it is desirable to use the compound in a small amount so far as the threshold voltage satisfies a required value. However, since the absolute value of the dielectric anisotropy of the compounds expressed by one of the general formulas (7) to (9) is smaller than 5, low voltage driving sometimes becomes impossible when the amount of the compounds becomes less than 40% by weight.

When liquid crystal compositions for TFT having a negative dielectric anisotropy value are produced, it is preferable to use the compound expressed by one of the general formulas (7) to (9) in a range of more than 40% by weight based on the total amount of liquid crystal composition and 50 to 95% by weight is preferable.

Also, for the purpose of improving the steepness of voltage-transmittance curve by controlling elastic constant, a compound expressed by one of the general formulas (7) to (9) is sometime added to liquid crystal compositions having a positive dielectric anisotropy value. In this case, the amount of the compound expressed by one of the general formulas (7) to (9) is preferably less than 30% by weight.

As preferable examples of the compounds used in the liquid crystal compositions of the present invention and expressed by one of the general formulas (10) to (12), the compounds of the following general formulas can be mentioned:

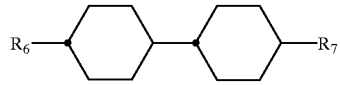
(10-1)

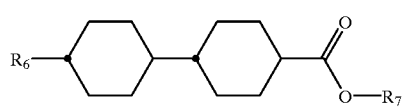
(10-2)

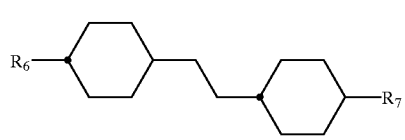
(10-3)

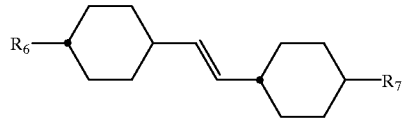
(10-4)

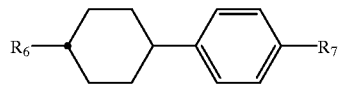
(10-5)

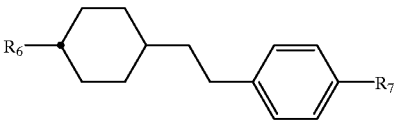
(10-6)

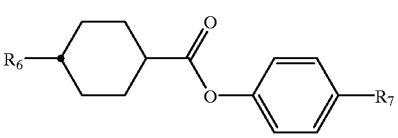
(10-7)

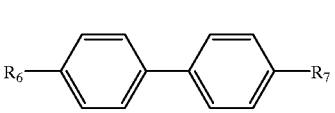
(10-8)

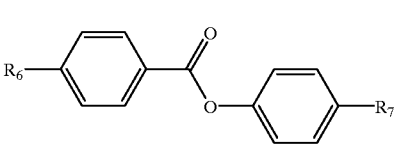
(10-9)

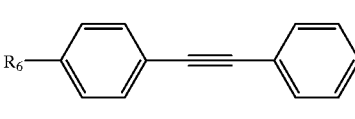
(10-10)

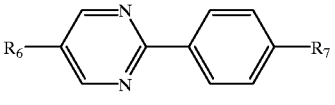
(10-11)

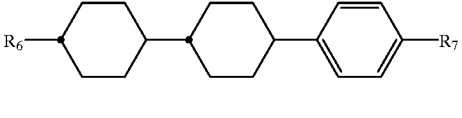
(11-1)

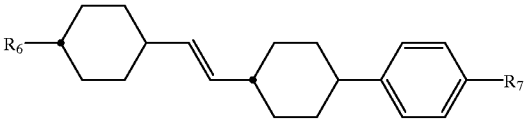
(11-2)

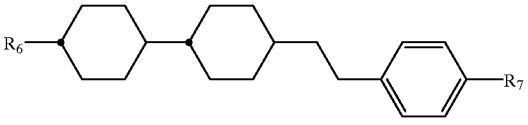
(11-3)

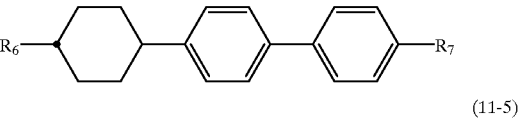
(11-4)

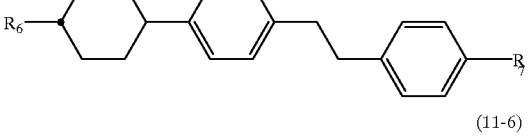
(11-5)

(11-6)

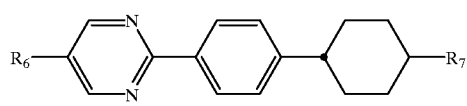
(11-7)

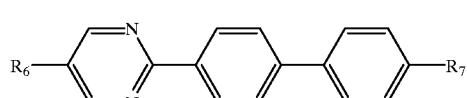
(11-8)

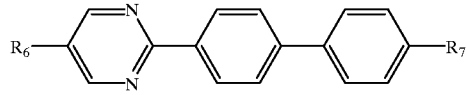
(11-9)

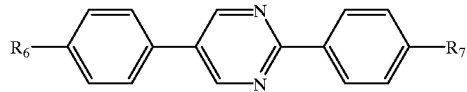
(11-10)

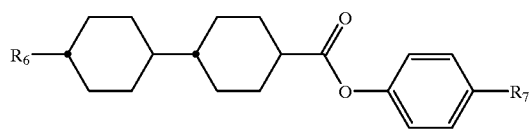
(11-11)

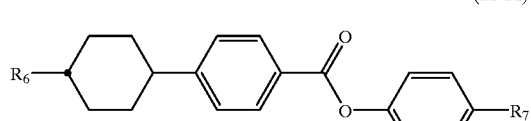
(11-12)

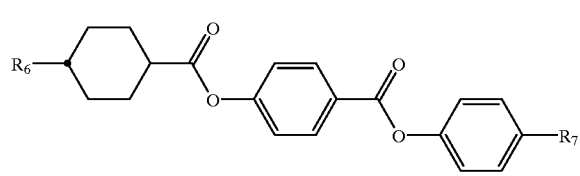
(11-13)

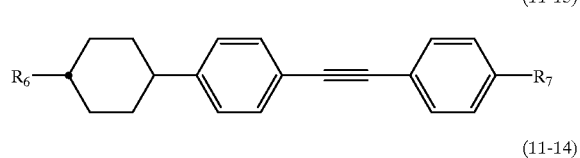
(11-14)

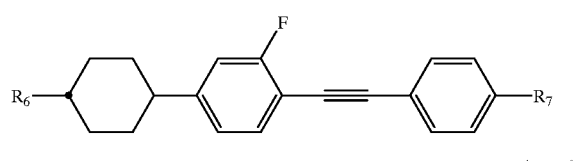
(11-15)

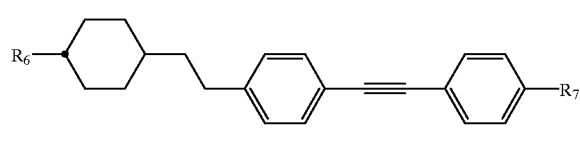
(11-16)

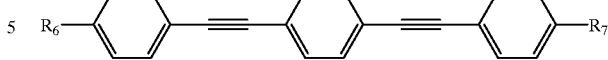
(11-17)

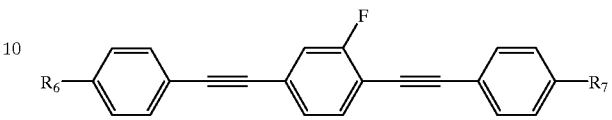
(11-18)

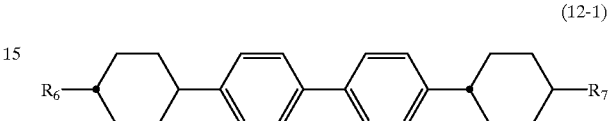
(12-1)

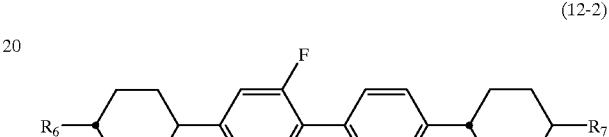
(12-2)

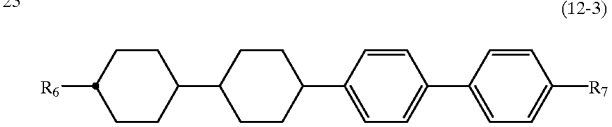
(12-3)

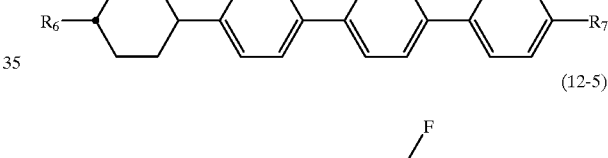
(12-4)

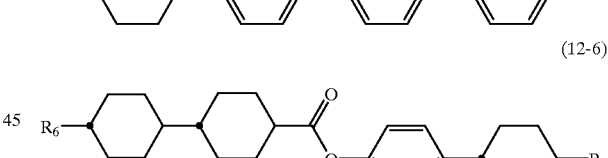
(12-5)

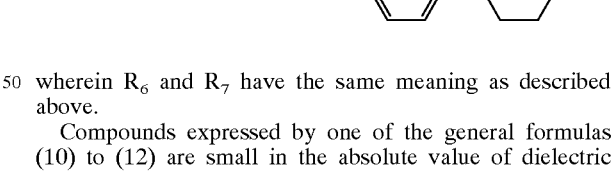
(12-6)

wherein $R_6$ and $R_7$ have the same meaning as described above.

Compounds expressed by one of the general formulas (10) to (12) are small in the absolute value of dielectric anisotropy and the value is close to zero. Compounds expressed by the general formula (10) are used principally for the purpose of adjusting viscosity or adjusting optical anisotropy value. Compounds expressed by the general formula (11) or (12) are used for the purpose of widening nematic range such as raising clearing point or for the purpose of adjusting optical anisotropy value.

When the amount of the compound expressed by one of the general formulas (10) to (12) is increased in liquid crystal compositions, threshold voltage of the liquid crystal compositions rises and viscosity lowers. Accordingly, it is desirable to use the compound in a large amount in the range wherein the threshold voltage of the liquid crystal compositions satisfies a required value. When liquid crystal compositions for TFT are produced, the amount of the compound expressed by one of the general formulas (10) to (12) is preferably less than 40% by weight in liquid crystal compositions and the amount is more desirably less than 35% by weight. Further, when liquid crystal compositions for STN or TN are produced, the amount of the compound expressed by one of the general formulas (10) to (12) is preferably less than 70% by weight in liquid crystal compositions and the amount is more desirably less than 60% by weight.

In liquid crystal compositions for STN, TFT, or others, an optically active compound is usually added for the purpose of inducing helical structure of liquid crystals to adjust required twist angle and to prevent reverse twist. Even in the liquid crystal compositions of the present invention, any of known optically active compounds can be added for such purposes. As examples of preferable optically active compounds, the compound of the following formulas can be mentioned:

Symbol: C15

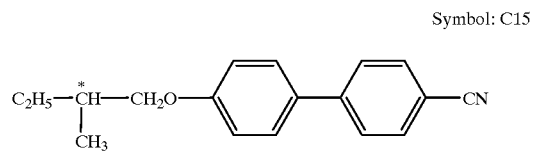

Symbol: CB15

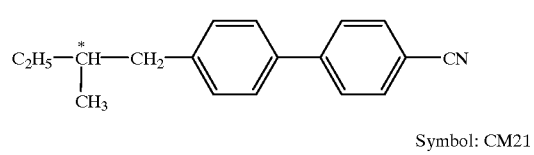

Symbol: CM21

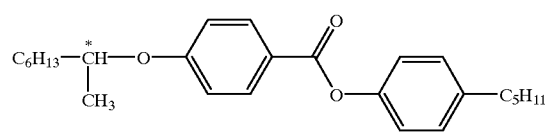

Symbol: CM33

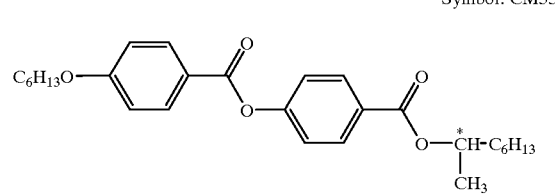

Symbol: CM43L

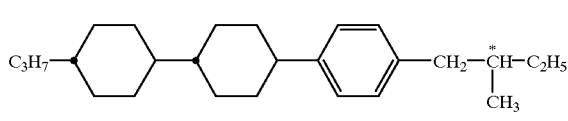

Symbol: CM45

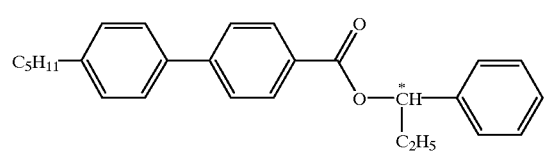

-continued

Symbol: CM47

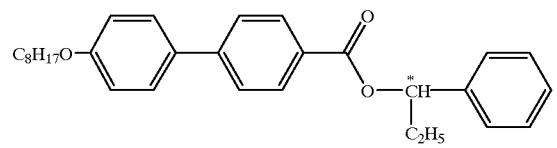

Symbol: CN

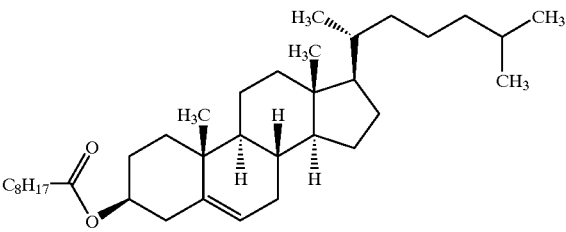

Usually, these optically active compounds are added to the liquid crystal compositions of the present invention to adjust the pitch of the twist. Pitch of the twist is preferably adjusted in the range of 40 to 200 μm in the case of liquid crystal compositions for TFT or TN, and preferably adjusted in the range of 6 to 20 μm in the case of liquid crystal compositions for STN. In the case of liquid crystal compositions for bistable TN, it is preferably adjusted in the range of 1.5 to 4 μm. Besides, two or more kind of optically active compounds may be added for the purpose of adjusting the dependency of the pitch on temperature.

Liquid crystal compositions of the present invention can be used as ones for GH (guest-host) mode by adding a dichroic dye such as merocyanine type, styryl type, azo type, azomethine type, azoxy type, quinophthalone type, anthraquinone type, and tetrazine type thereto. Further, the liquid crystal compositions can be used as NCAP which is prepared by the microencapsulation of a nematic liquid crystal, or as liquid crystal compositions for polymer dispersed liquid crystal display devices (PDLCD) represented by polymer net work liquid crystal display devices (PNLCD) prepared by forming a polymer of three-dimensional reticulated structure in a liquid crystal. Still further, the liquid crystal compositions of the present invention can be used as ones for ECB (electrically controlled birefringence) mode or dynamic scattering (DS) mode.

Liquid crystal compositions of the present invention can be produced by conventional methods. Generally, a method in which various components are dissolved in one another at a high temperature is adopted.

BEST MODE FOR CARRYING OUT THE INVENTION

The present invention will be described in more detail below with reference to Examples.

EXAMPLE 1

Preparation of 2,2', 3'-trifluoro-4'-ethoxy-4-(4-propylcyclohexyl)biphenyl [Compound expressed by the general formula (1) wherein Ra is propyl group, Rb is ethoxy group, ring $A_1$ is cyclohexane-1,4-diyl, ring $A_2$ is 2,3-difluorophenyl, xb is fluorine atom, all of Xa, Xc, and Xd are hydrogen atoms, and both $Z_1$ and $Z_2$ are single bonds; Compound No. 22]

First Step

To a mixture of metal magnesium (1.0 mol) and 100 ml of tetrahydrofuran (THF) was slowly added dropwise a solution of 3-fluorophenyl bromide (1.0 mol) in 650 ml of THF at a temperature of lower than 5° C. and then stirred (for about 2 hours) until the metal magnesium was completely consumed to obtain a grey solution of a Grignard reagent in THF. While maintaining the solution at a temperature of lower than 0° C., solution of 4-propylcyclohexanone (1.0 mol) in 500 ml of THF was gradually added thereto and stirred at 23° C. for 3 hours.

To this reaction solution was added 300 ml of saturated aqueous ammonium chloride solution and sufficiently stirred. It was extracted twice with 200 ml of ethyl acetate and the organic layer was dried over anhydrous magnesium sulfate. The solid substances were filtered off and the solvent was removed under a reduced pressure to obtain an red oily residue.

To this residue were added 500 ml of toluene and p-toluenesulfonic acid (0.1 mol) and then refluxed for 3 hours while being stirred and while the water generated was being removed. Having confirmed the fact that the water ceased to generate, the reaction solution was cooled down to room temperature. To the yellow homogeneous reaction solution thus obtained was added 300 ml of saturated aqueous sodium bicarbonate solution, and sufficiently stirred. The separated toluene layer was washed with 300 ml of water and dried over magnesium sulfate.

The solid substances were filtered off and the toluene was removed under a reduced pressure. The red oily residue thus obtained was subjected to silica gel column chromatography (eluent: heptane), and then the solvent was removed under a reduced pressure to obtain a pale yellow oily 4-propyl-1-(3-fluorophenyl)cyclohexene (0.76 mol).

Second Step

A mixture of 4-propyl-1-(3-fluorophenyl)cyclohexene (0.75 mol), 450 ml of ethanol, and 30 g of 5%-PdC was stirred under hydrogen gas atmosphere for 7 hours. Having confirmed the fact that the reaction system ceased to absorb the hydrogen gas, the palladium catalyst was removed by filtration. The filtrate was concentrated under a reduced pressure to obtain colorless oily residue. This residue was subjected to a distillation under a reduced pressure, and the fractions of distillate at 120 to 131° C. at 5 mmHg were collected. By $^1$H-NMR, these fractions were confirmed to be 4-(3-fluorophenyl)propylcyclohexane (0.7 mol). While these fractions were confirmed to be a mixture of cis/trans (55%/45%) by GLC analysis, the cis/trans mixture was used as it was in subsequent reactions.

To 4-(3-fluorophenyl)propylcyclohexane (0.3 mol) was added 400 ml of THF, and the colorless homogeneous solution thus obtained was cooled down to −68° C. To this solution was added dropwise cyclohexane solution (1.06 M solution) of a commercially available sec-butyl lithium in an amount of corresponding to 0.33 mol in 3 hours while maintaining the same temperature. Further, it was stirred for 1 hour and then solution of iodine (0.31 mol) in 250 ml of THF was added dropwise thereto at a temperature which does not exceed −60° C. The reaction solution was colorless and transparent at the beginning, but changed to red at the time when the addition of iodine (0.3 mol) was finished. The reaction solution was gradually warmed up to room temperature and further stirred for a whole day and night.

To the reaction solution was added 100 ml of toluene, and the solution was washed with 500 ml of water, 400 ml of saturated aqueous sodium thiosulfate solution, and 400 ml of saturated aqueous sodium chloride solution in turn, and dried over anhydrous magnesium sulfate. Solid substances were filtered off, and the solution thus obtained was concentrated under a reduced pressure to obtain a highly viscous, yellow, and oily residue. By having been allowed to stand, this product became crystals.

The crystals thus obtained were washed with 100 ml of ethanol and recrystallized from 50 ml of heptane. By $^1$H-NMR, the crystals were confirmed to be 4-(3-fluoro-4-iodophenyl)-propylcyclohexane (0.24 mol). Further, it was confirmed by GLC that the crystals had a purity of 97.9% and contained 2.1% of unreacted compound, 4-(3-fluorophenyl)propylcyclohexane.

Third Step

To 2,3-difluoroethoxybenzene (0.4 mol) was added 200 ml of THF and cooled down to −70° C. Cyclohexane solution (1.06M solution) of sec-butyl lithium in an amount of corresponding to 0.44 mol was added thereto while the reaction system was being maintained at a temperature lower than −65° C. After it was stirred for 20 minutes, solution of triisopropyl borate (0.6 mol) in 50 ml of THF was added at a temperature of −68 to −70° C., and stirred for 3 hours.

The reaction product was gradually warmed up to room temperature (about 18° C.), 100 ml of 6M hydrochloric acid was added thereto, and the solution was stirred for 30 minutes. The reaction solution was extracted thrice with 300 ml of diethyl ether. After the extracts were combined and washed with 100 ml of saturated aqueous sodium chloride solution, diethyl ether layer was dried over anhydrous sodium sulfate. After solid substances were removed, it was concentrated under a reduced pressure to obtain a brown solid. This product was sufficiently washed with 100 ml of heptane to obtain pale brown, powder-like crystals of 2,3-difluoro-4-ethoxyphenyl boric acid (0.29 mol).

Fourth Step

A mixture of the 4-(3-fluoro-4-iodophenyl) propylcyclohexane (0.05 mol) and the 2,3-difluoro-4-ethoxyphenyl boric acid (0.075 mol) both prepared by previous steps, sodium carbonate (0.2 mol), 2 g of 5%-Pdc, 50 ml of toluene, 50 ml of ethanol, and 7 ml of water was refluxed for 8 hours. After it was cooled down to room temperature, the catalyst was filtered off, and the filtrate was concentrated under a reduced pressure. The residue thus obtained was purified by subjecting it to silica gel column chromatography (eluent: heptane/toluene=10/1 mixed solvent) and then recrystallizing from 100 ml of ethanol to obtain a white solid of the subject compound (0.031 mol).

Nuclear magnetic resonance spectrums of this product were shown below.

$^1$H-NMR (CDCl$_3$) δ: 7.34–6.68 (m, 5H), 4.15 (q, 2H), 2.51 (t, 1H), 2.51–1.39 (m, 16H), 0.96 (t, 3H); $^{19}$F-NMR (CDCl$_3$) δ: −116.2, −138.6, −158.8.

This product exhibited a liquid crystallinity and its phase transition temperatures were as follows: Melting point (Cr)= 92.0° C. Nematic phase-isotropic liquid phase (T$_{NI}$)=128.1° C.

EXAMPLE 2 (USE EXAMPLE 1)

Liquid crystal composition (A) comprising the following liquid crystal compounds in the amount shown below was prepared.

4-ethoxyphenyl=4-propylcyclohexane carboxylate 17.2%

4-butoxyphenyl=4-propylcyclohexane carboxylate 27.6%

4-ethoxyphenyl=4-butylcyclohexane carboxylate 20.7%

4-methoxyphenyl=4-pentylcyclohexane carboxylate 20.7%

4-ethoxyphenyl=4-pentylcyclohexane carboxylate 13.8%

Physical property values of this liquid crystal composition (A) were as follows:

$T_{NI}$=74.0° C.

Δε=−1.3

Δn=0.087

Physical property values of the liquid crystal composition (B) which comprises 85% by weight of the liquid crystal composition (A) described above and 15% by weight of the 2,2',3'-trifluoro-4'-ethoxy-4-(4-propylcyclohexyl)biphenyl obtained in Example 1 were as follows. Values in the parentheses indicate the values of 2,2',3'-trifluoro-4'-ethoxy-4-(4-propylcyclohexyl)biphenyl calculated by extrapolation from the mixing ratio.

$T_{NI}$=80.0° C.

Δε=−2.16 (−7.37)

Δn=0.097 (0.155)

COMPARATIVE EXAMPLE 1

According to the disclosures by V. Reiffenrath et al. described above, 2,3-difluoro-4-ethoxy-4'-(4-propylcyclohexyl)-biphenyl was prepared. Phase transition temperatures of this compound were as follows:

Cr=80.0° C.

$T_{NI}$=174.7° C.

Extrapolated values from the physical property values of the liquid crystal composition comprising 85% by weight of the liquid crystal composition (A) described above and 15% by weight of the compound of Comparative Example 1 were as follows:

Δε=−5.90

Δn=0.188

From the comparison between Example 2 and Comparative Example 1, it can be confirmed that the compounds of the present invention combine a large dielectric anisotropy value with a small optical anisotropy value compared with heretofore known compounds.

EXAMPLE 3

According to the method in Example 1 and the preparation methods described above, following compounds (Compound No. 1 through Compound No. 123) were prepared. Among the physical property values additionally shown below, transition temperatures indicate the phase transition temperatures of a particular compound itself, Δε and Δn indicate the extrapolated values calculated from the physical property values of the liquid crystal composition obtained by mixing the liquid crystal composition (A) described above with 15% by weight of the particular compound.

1

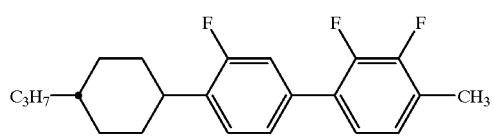

2

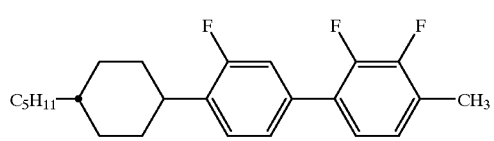

3

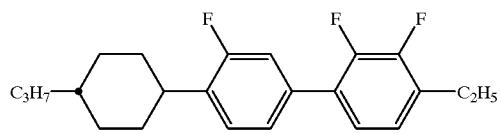

4

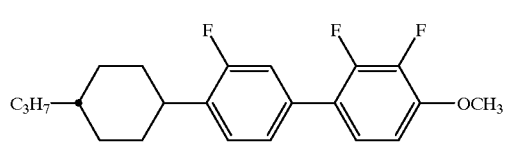

5

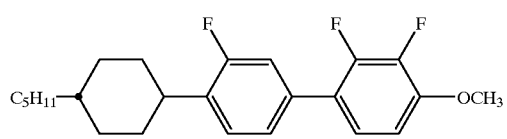

6

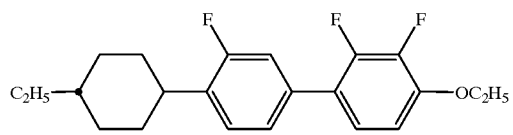

7

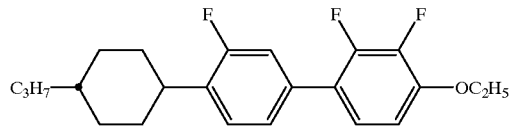

C 71.4 N 148.8 I
Δε: −6.84, Δn: 0.176

8

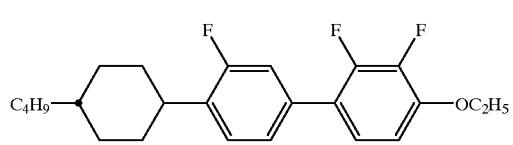

9

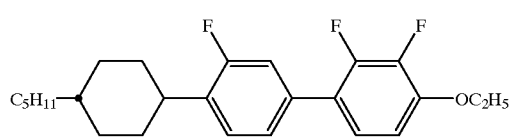

10

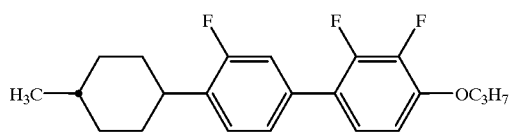

11

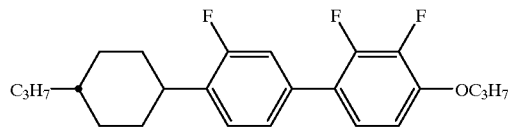

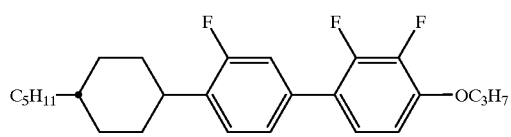
12
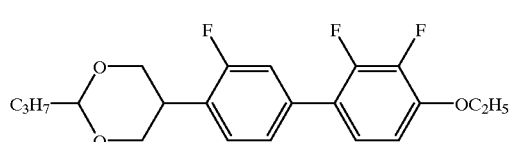
13
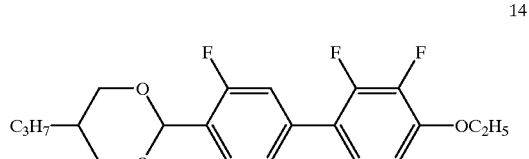
14
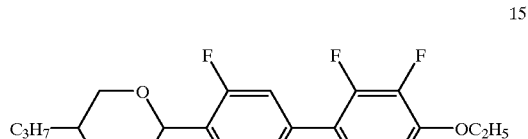
15
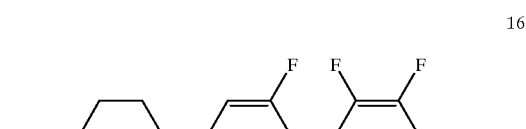
16
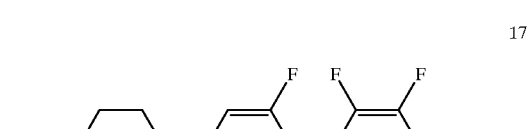
17
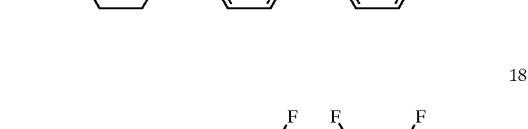
18
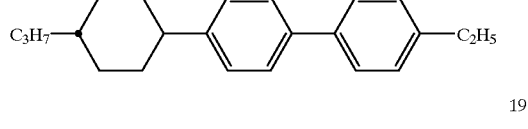
19
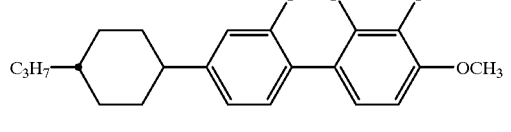
20
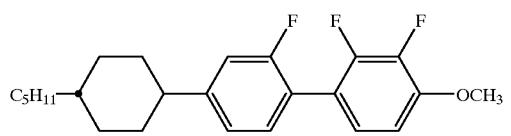
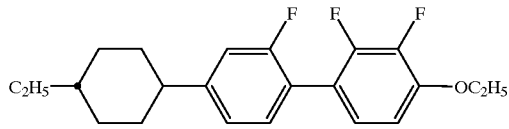
21
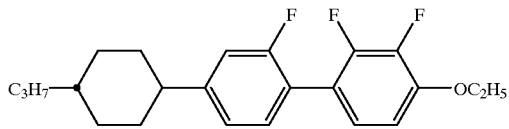
22
C 92.0 N 128.1 I
Δε: −7.4, Δn: 0.155
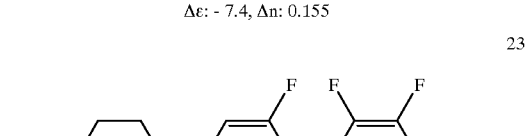
23
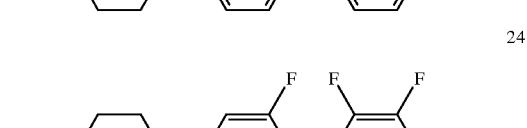
24
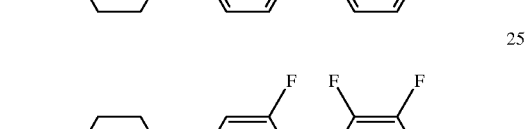
25
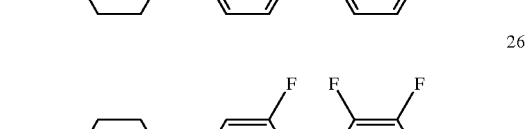
26
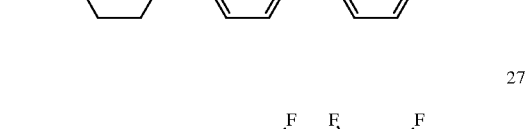
27
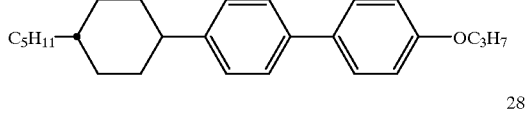
28
29

30
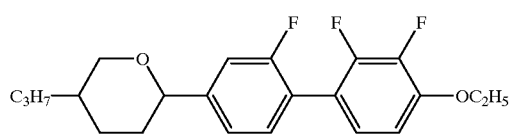
31
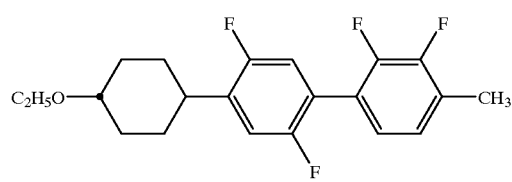
32
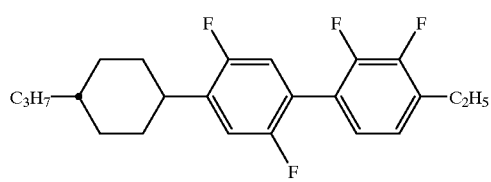
33
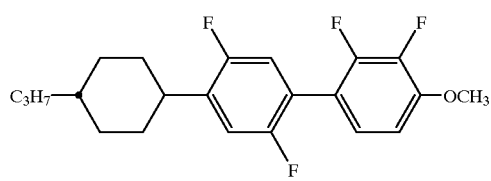
34
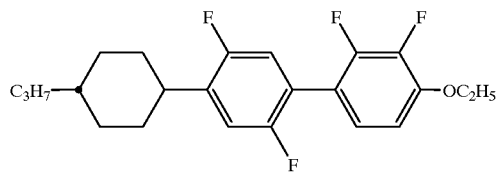
C 109.8 N 114.4 I
35
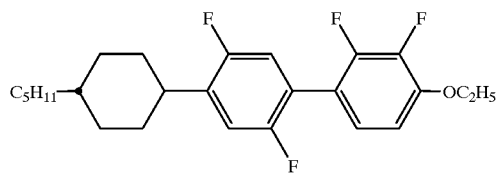
36
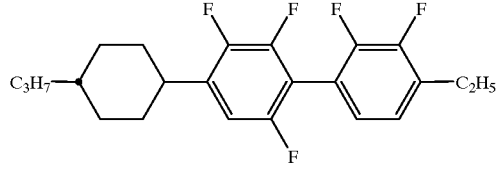
37
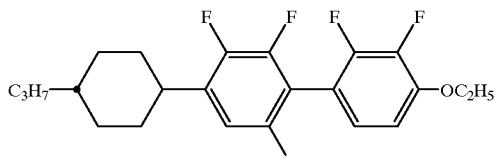
38
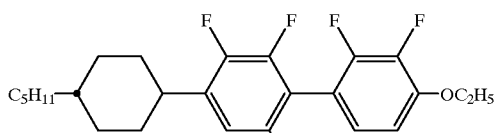
39
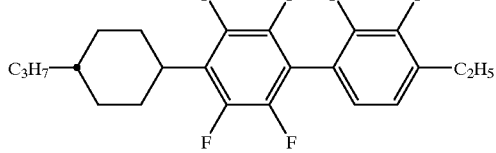
40
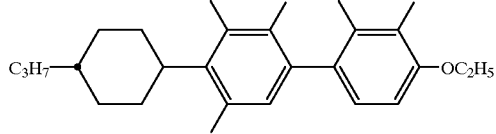
41
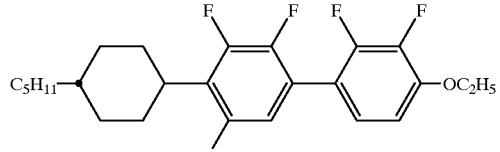
42
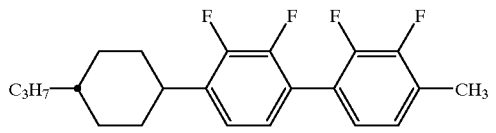
43
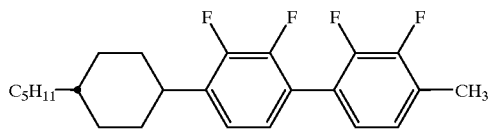
44
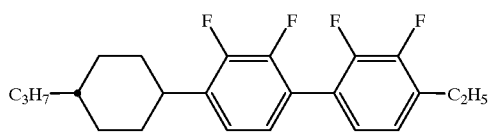

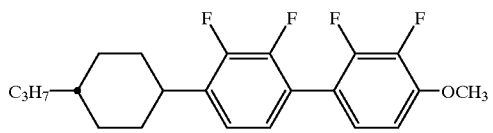
45
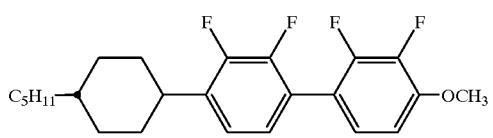
46
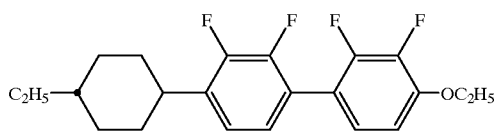
47
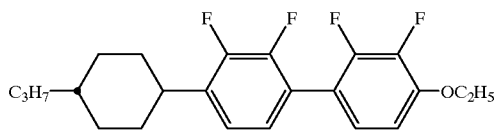
48
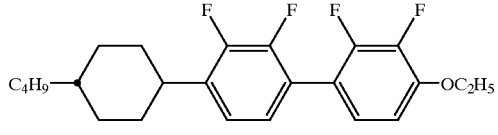
49
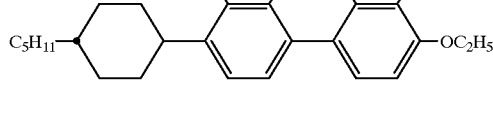
50
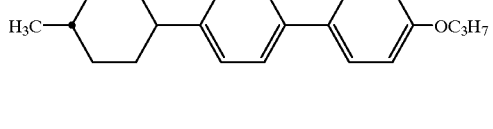
51
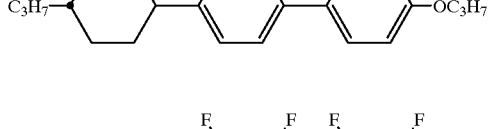
52
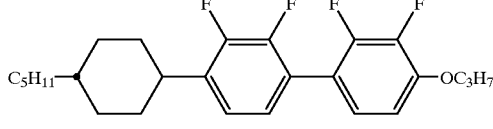
53
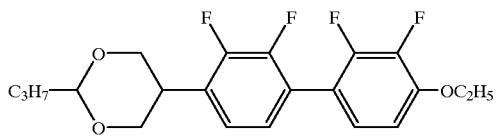
54
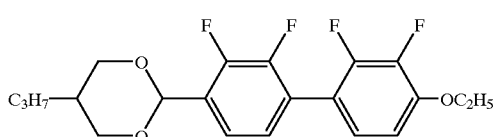
55
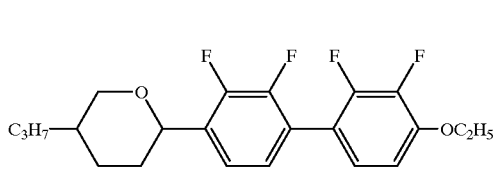
56
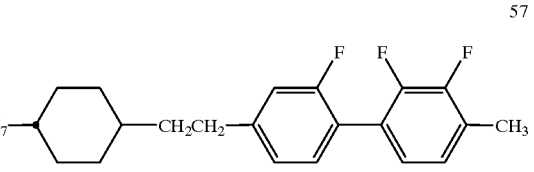
57
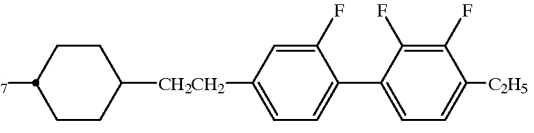
58
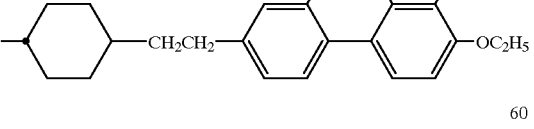
59
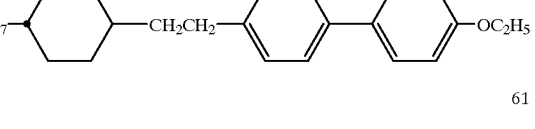
60
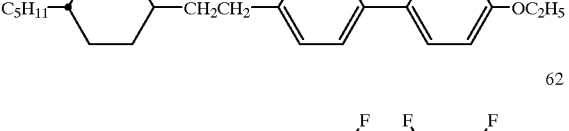
61
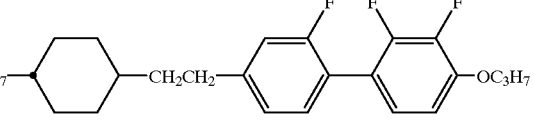
62

63
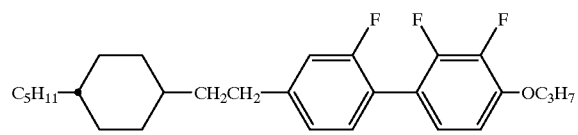
64
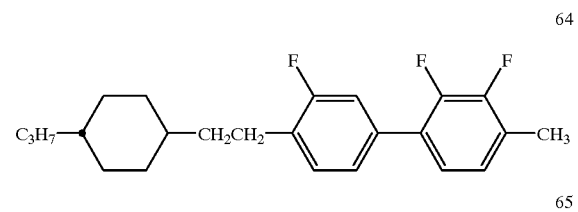
65
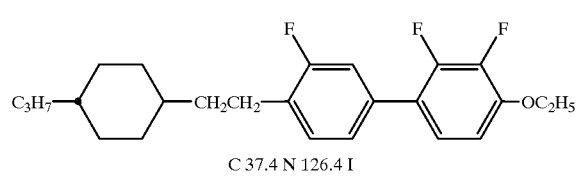
C 37.4 N 126.4 I
66
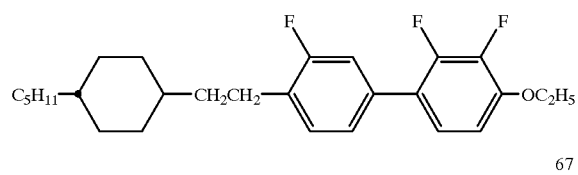
67
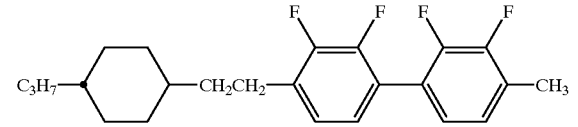
68
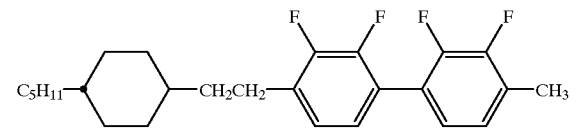
69
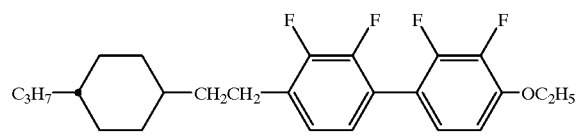
70
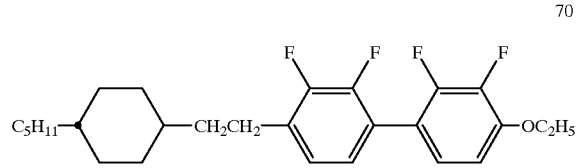
71
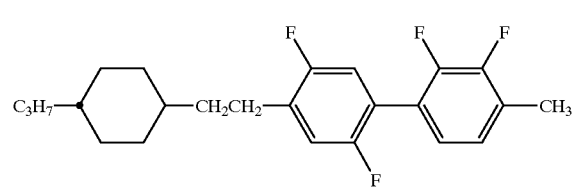
72
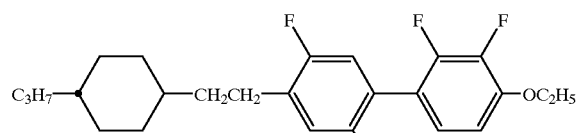
73
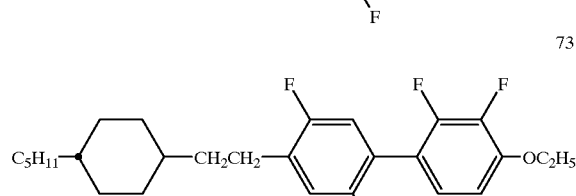
74
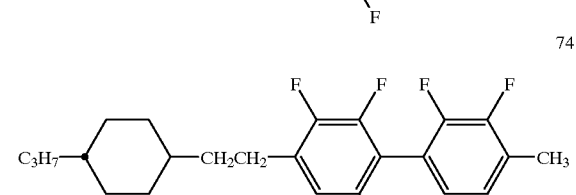
75
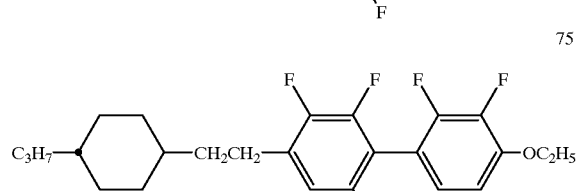
76
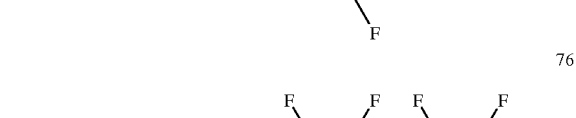
77
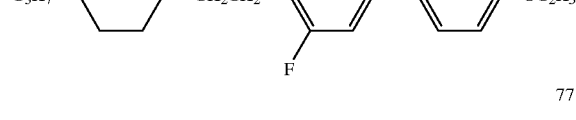
78
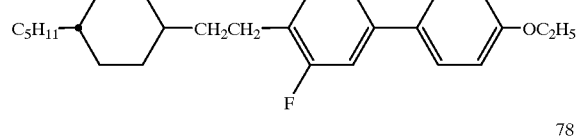
79
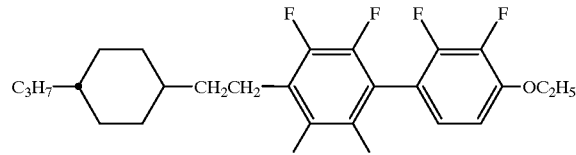

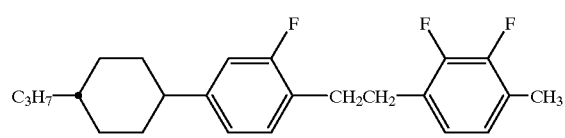
80
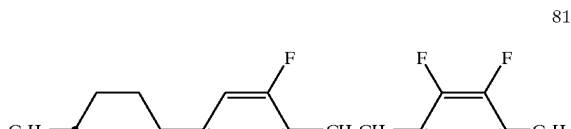
81
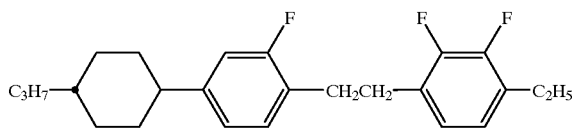
82
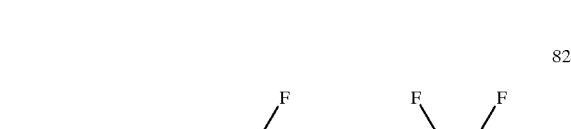
83
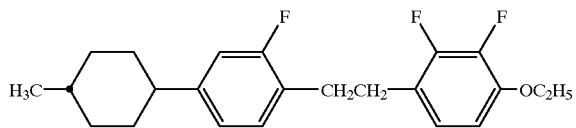
84
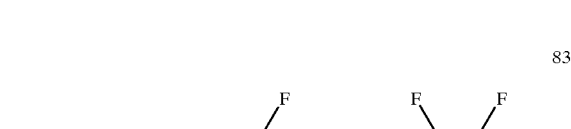
85
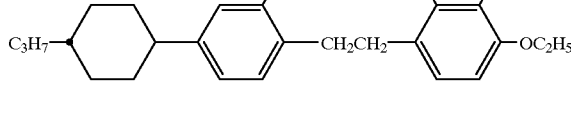
86
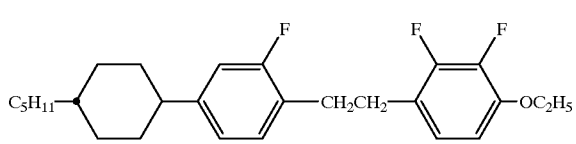
87
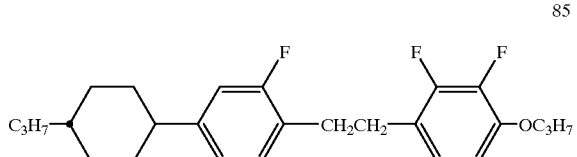
88
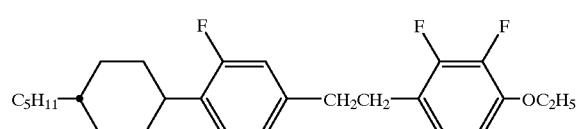
89
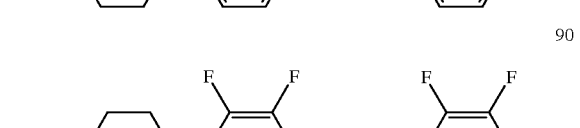
90
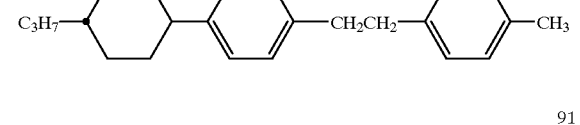
91
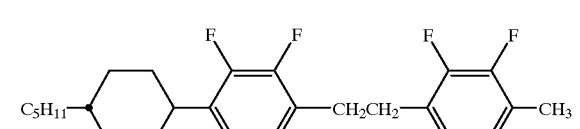
92
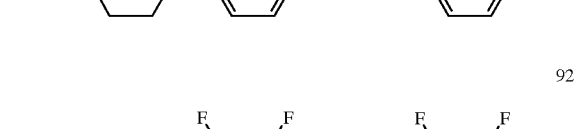
93
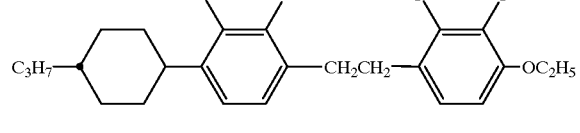
94
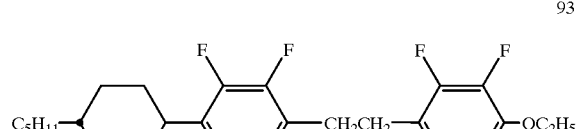
95
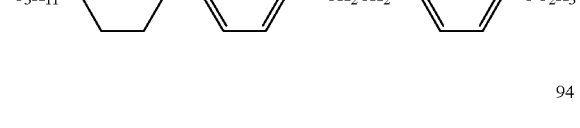
96
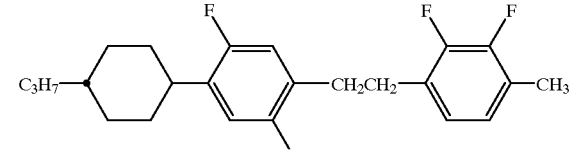

97
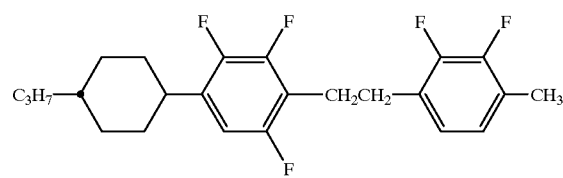
98
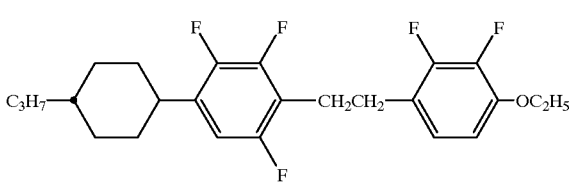
99
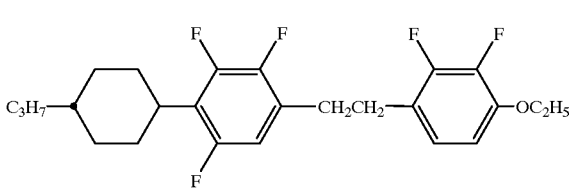
100
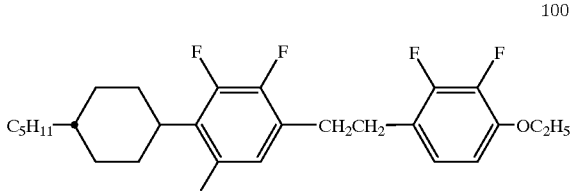
101
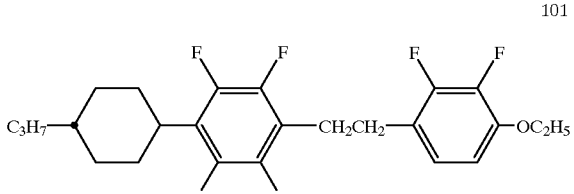
102
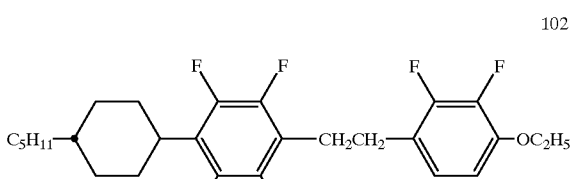
103
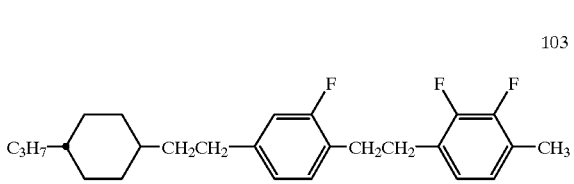
104
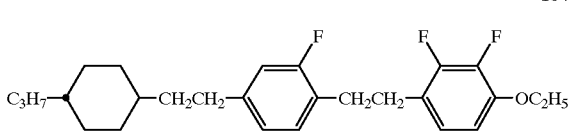
105
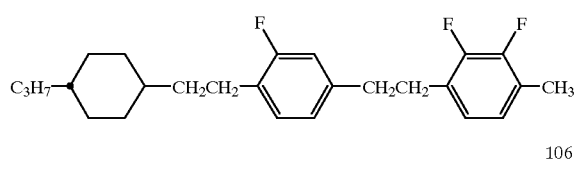
106
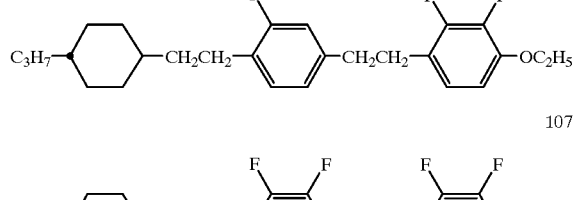
107
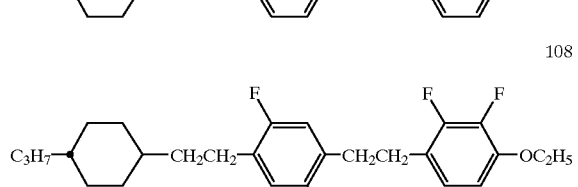
108
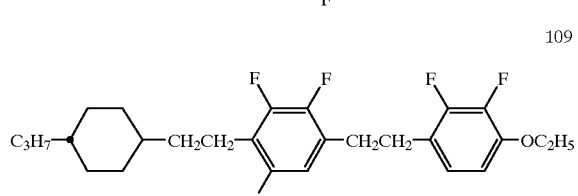
109
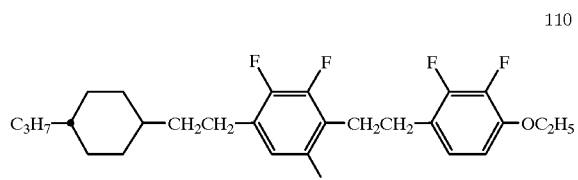
110
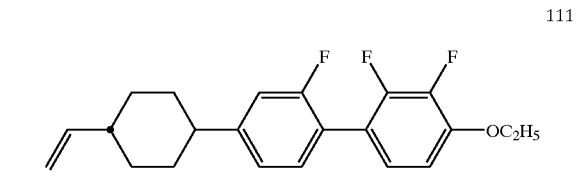
111
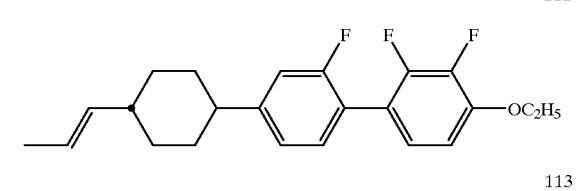
112
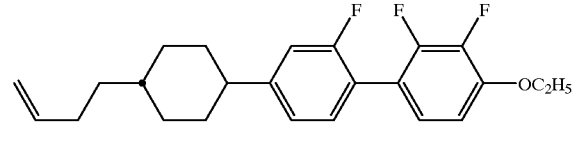
113

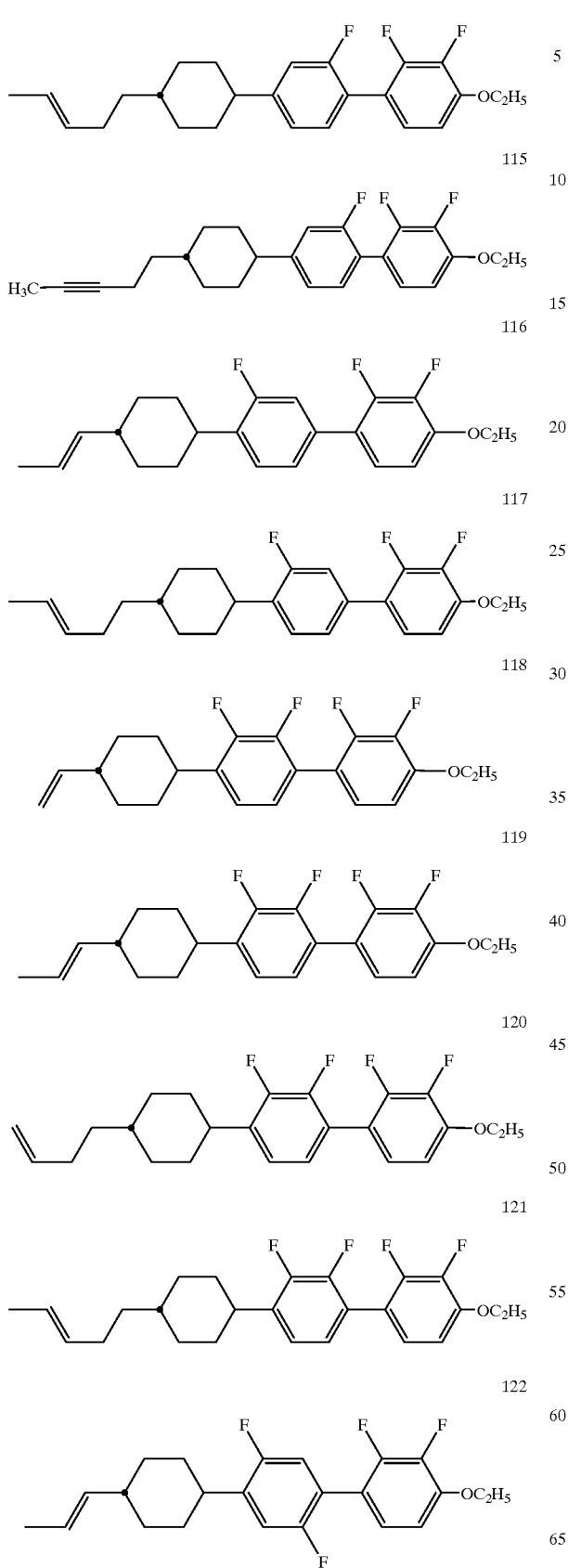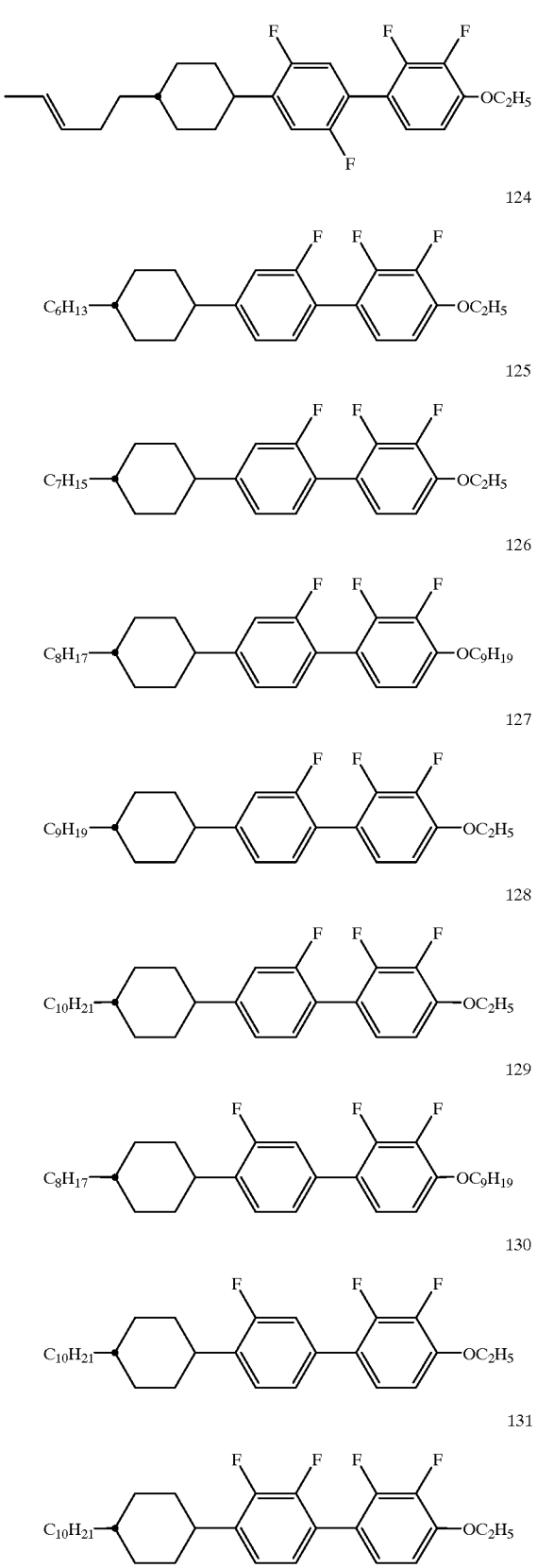

132
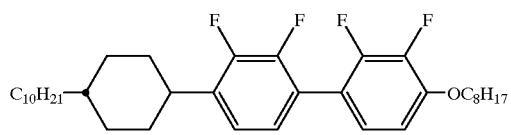
133
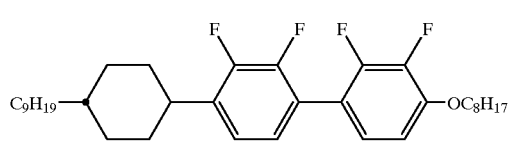
134
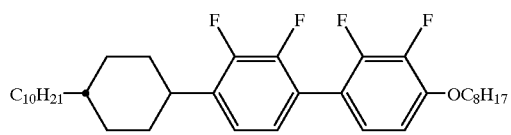
135
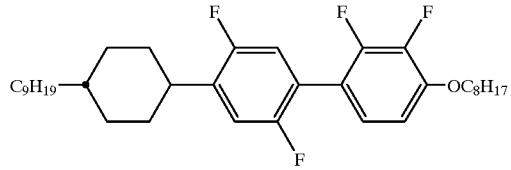
136
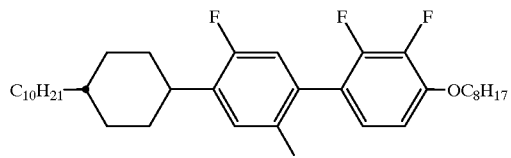
137
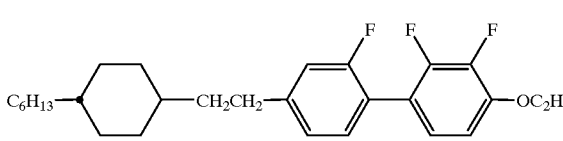
138
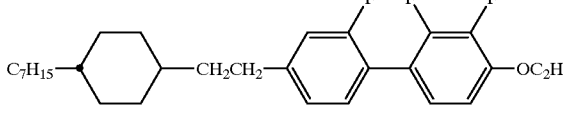
139
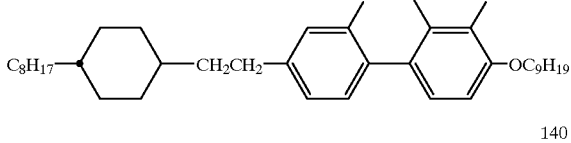
140
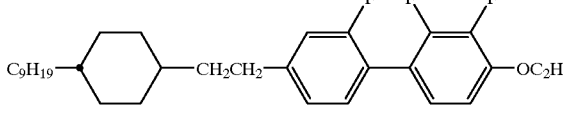
141
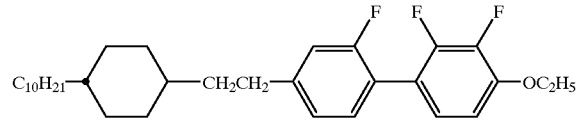
142
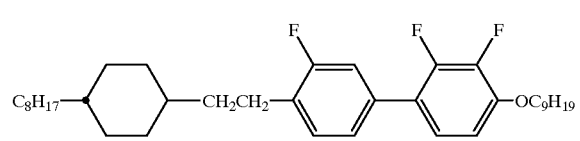
143
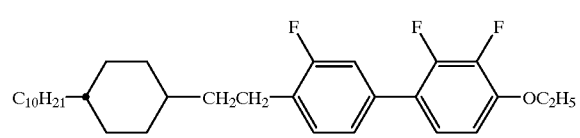
144
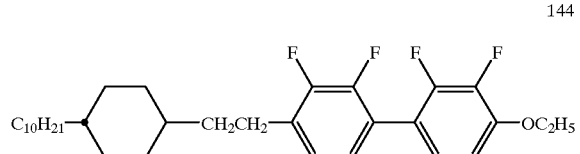
145
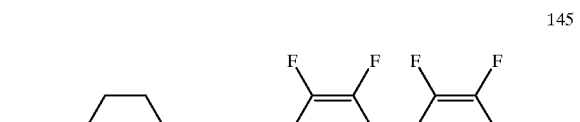
146
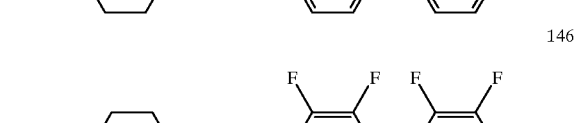
147
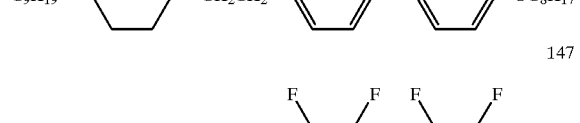
148
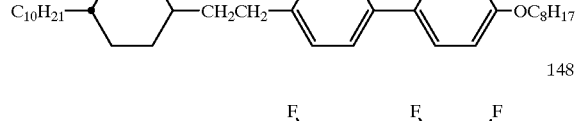
149
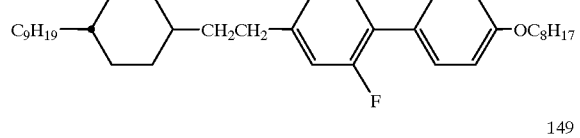
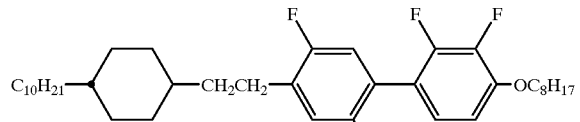
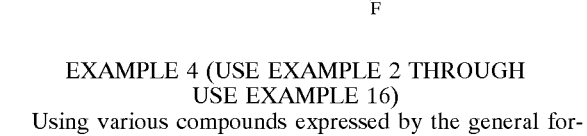
EXAMPLE 4 (USE EXAMPLE 2 THROUGH USE EXAMPLE 16)
Using various compounds expressed by the general formula (1), liquid crystal compositions shown in Use Example 2 through Use Example 16 were prepared. In the following, "%" means % by weight unless otherwise specified, and when cis-trans isomers exist in a particular compound, the compound used was trans- form. Further, the compounds in the following use examples are designated by symbols according to the definitions shown in the following Table 1 and Table 2. Viscosity (η) was determined at 20° C.

TABLE 1

| Left side terminal | Symbol |
|---|---|
| $C_nH_{2n+1}$— | n— |
| $C_nH_{2n+1}O$— | nO— |
| $C_nH_{2n+1}OC_mH_{2m}$— | nOm— |
| $CH_2=CH$— | V— |
| $CH_2=CHC_nH_{2n}$— | Vn— |
| $C_nH_{2n+1}CH=CH$— | nV— |
| $C_nH_{2n+1}CH=CHC_mH_{2m}$— | nVm— |
| $C_nH_{2n+1}CH=CHC_mH_{2m}CH=CHC_kH_{2k}$— | nVmVk— |
| $CF_2=CH$— | VFF— |

| Bonding group | Symbol |
|---|---|
| —$CH_2CH_2$— | 2 |
| —$(CH_2)_4$— | 4 |
| —COO— | E |
| —C≡C— | T |
| —CH=CH— | V |
| —$CF_2O$— | CF2O |
| —$OCF_2$— | OCF2 |

| Ring structure | Symbol |
|---|---|
|  | B |
| 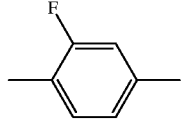 | B(2F) |
|  | B(2F,5F) |
| 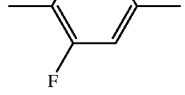 | B(2F,3F,6F) |
| 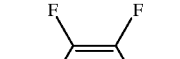 | B(F,F) |
| 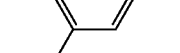 | Py |

TABLE 1-continued

| | |
|---|---|
| 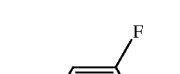 | B(2CN,3CN) |
| 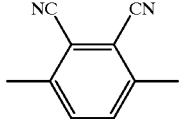 | B(F) |
| 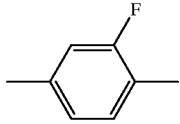 | B(2F,3F) |
| 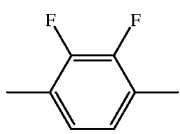 | B(2F,3F,5F) |
| 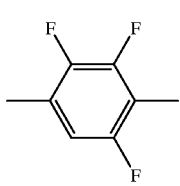 | B(2F,3F,5F,6F) |
| 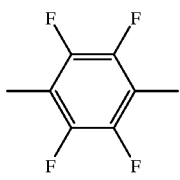 | H |
| 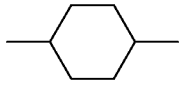 | Pr(F) |

TABLE 2

| Right side terminal group | Symbol |
|---|---|
| —F | —F |
| —Cl | —CL |
| —CN | —C |
| —$CF_3$ | —CF3 |
| —$OCF_3$ | —OCF3 |
| —$OCF_2H$ | —OCF2H |
| —$C_nH_{2n+1}$ | —n |
| —$OC_nH_{2n+1}$ | —On |
| —$COOCH_3$ | —EMe |
| —CH=$CH_2$ | —V |
| —$(CH_2)_nCH=CH_2$ | —nV |
| —$(CH_2)_nCH=CHC_mH_{2m+1}$ | —nVm |
| —C≡C—CN | —TC |
| —CH=$CF_2$ | —VFF |
| —$(CH_2)_nCH=CF_2$ | —nVFF |
| —CH=$CHC_nH_{2n}F$ | —VnF |

Use Example 2

| | |
|---|---|
| 3-HB(F)B(2F,3F)-O2 | 7.0% |
| 3-HB(2F)B(2F,3F)-O2 | 7.0% |
| 3-HEB-O4 | 28.0% |
| 4-HEB-O2 | 20.0% |
| 5-HEB-O1 | 20.0% |
| 3-HEB-O2 | 18.0% |

$T_{NI} = 82.3$ (° C.)
$\eta = 23.9$ (mPa · s)
$\Delta n = 0.102$
$\Delta \epsilon = -2.1$ Use Example 3

| | |
|---|---|
| 3-HB(2F,5F)B(2F,3F)-O2 | 7.0% |
| 3-H2B(2F)B(2F,3F)-O2 | 7.0% |
| 3-HH-2 | 5.0% |
| 3-HH-4 | 6.0% |
| 3-HH-O1 | 4.0% |
| 3-HH-O3 | 5.0% |
| 5-HH-O1 | 4.0% |
| 3-HB(2F,3F)-O2 | 12.0% |
| 5-HB(2F,3F)-O2 | 11.0% |
| 5-HHB(2F,3F)-O2 | 15.0% |
| 3-HHB(2F,3F)-2 | 24.0% |

$T_{NI} = 78.2$ (° C.)
$\Delta n = 0.091$
$\Delta \epsilon = -4.1$

Use Example 4

| | |
|---|---|
| 3-HB(F)B(2F,3F)-O2 | 4.0% |
| 3-HB(2F)B(2F,3F)-O2 | 4.0% |
| 3-H2B(2F)B(2F,3F)-O2 | 4.0% |
| 3-HH-4 | 5.0% |
| 3-HH-5 | 5.0% |
| 3-HH-O1 | 6.0% |
| 3-HH-O3 | 6.0% |
| 3-HB-O1 | 5.0% |
| 3-HB-O2 | 5.0% |
| 3-HB(2F,3F)-O2 | 10.0% |
| 5-HB(2F,3F)-O2 | 10.0% |
| 5-HHB(2F,3F)-O2 | 13.0% |
| 3-HHB(2F,3F)-2 | 4.0% |
| 3-HHB(2F,3F)-2 | 4.0% |
| 3-HHEH-3 | 5.0% |
| 3-HHEH-3 | 5.0% |
| 3-HHEH-3 | 5.0% |

$T_{NI} = 81.5$ (° C.)
$\Delta n = 0.083$
$\Delta \epsilon = -3.5$

Use Example 5

| | |
|---|---|
| 3-HB(F)B(2F,3F)-O2 | 4.0% |
| 3-HB(2F)B(2F,3F)-O2 | 4.0% |
| 3-HB(2F,5F)B(2F,3F)-O2 | 4.0% |
| 3-H2B(2F)B(2F,3F)-O2 | 4.0% |
| 3-BB(2F,3F)-O2 | 12.0% |
| 3-BB(2F,3F)-O4 | 10.0% |
| 5-BB(2F,3F)-O4 | 10.0% |
| 2-BB(2F,3F)B-3 | 25.0% |
| 3-BB(2F,3F)B-5 | 13.0% |
| 5-BB(2F,3F)B-5 | 14.0% |

$T_{NI} = 85.8$ (° C.)
$\Delta n = 0.200$
$\Delta \epsilon = -4.2$

Use Example 6

| | |
|---|---|
| 3-HB(F)B(2F,3F)-O2 | 6.0% |
| 3-BB(2F,3F)-O2 | 10.0% |
| 5-BB-5 | 9.0% |
| 5-BB-O6 | 9.0% |
| 5-BB-O8 | 8.0% |
| 1-BEB-5 | 6.0% |
| 3-BEB-5 | 6.0% |
| 5-BEB-5 | 3.0% |
| 3-HEB-O2 | 20.0% |
| 5-BBB(2F,3F)-7 | 3.0% |
| 3-H2BB(2F)-5 | 20.0% |

$T_{NI} = 80.2$ (° C.)
$\Delta n = 0.149$
$\Delta \epsilon = -3.0$

Use Example 7

| | |
|---|---|
| 3-HB(2F)B(2F,3F)-O2 | 9.0% |
| 3-HB-O1 | 15.0% |
| 3-HB-O2 | 6.0% |
| 3-HEB(2F,3F)-O2 | 9.0% |
| 4-HEB(2F,3F)-O2 | 9.0% |
| 2-BB2B-O2 | 6.0% |
| 3-BB2B-O2 | 6.0% |
| 5-BB2B-O1 | 6.0% |
| 5-BB2B-O2 | 6.0% |
| 1-B2BB(2F)-5 | 7.0% |
| 3-B2BB(2F)-5 | 7.0% |
| 5-B(F)BB-O2 | 7.0% |
| 3-BB(2F,3F)B-3 | 7.0% |

$T_{NI} = 89.0$ (° C.)
$\eta = 24.2$ (mPa · s)
$\Delta n = 0.170$
$\Delta \epsilon = -2.0$ Example 8

| | |
|---|---|
| 3-HB(F)B(2F,3F)-O2 | 5.0% |
| 3-H2B(2F)B(2F,3F)-O2 | 5.0% |
| 3-HB-O1 | 9.0% |
| 3-HB-O2 | 9.0% |
| 3-HB-O4 | 9.0% |
| 2-BTB-O1 | 5.0% |
| 1-BTB-O2 | 5.0% |
| 3-BTB(2F,3F)-O2 | 13.0% |
| 5-BTB(2F,3F)-O2 | 13.0% |
| 3-B(2F,3F)TB(2F,3F)-O4 | 4.0% |
| 5-B(2F,3F)TB(2F,3F)-O4 | 4.0% |
| 3-HBTB-O1 | 5.0% |
| 3-HHB(2F,3F)-O2 | 6.0% |
| 5-HBB(2F,3F)-O2 | 5.0% |
| 5-BPr(F)-O2 | 3.0% |

$T_{NI} = 78.7$ (° C.)
$\eta = 28.5$ (mPa · s)
$\Delta n = 0.208$

Use Example 9

| | |
|---|---|
| 3-HB(2F)B(2F,3F)-O2 | 6.0% |
| 3-H2B(2F)B(2F,3F)-O2 | 6.0% |
| 3-HB-O2 | 10.0% |
| 5-HB-3 | 8.0% |
| 5-BB(2F,3F)-O2 | 10.0% |
| 3-HB(2F,3F)-O2 | 10.0% |
| 5-HB(2F,3F)-O2 | 8.0% |
| 5-HHB(2F,3F)-O2 | 4.0% |
| 5-HHB(2F,3F)-1O1 | 4.0% |
| 2-HHB(2F,3F)-1 | 5.0% |
| 3-HHB(2F,3F)-1 | 5.0% |
| 3-HBB-2 | 6.0% |
| 3-BB(2F,3F)B-3 | 8.0% |
| 5-B2BB(2F,3F)-O2 | 10.0% |

$T_{NI} = 69.0$ (° C.)
$\Delta n = 0.135$
$\Delta \epsilon = -4.1$

Use Example 10

| | |
|---|---|
| 3-HB(F)B(2F,3F)-O2 | 3.0% |
| 3-HB(2F)B(2F,3F)-O2 | 4.0% |
| 3-HB(2F,5F)B(2F,3F)-O2 | 3.0% |
| 3-H2B(2F)B(2F,3F)-O2 | 2.0% |
| 3-HB-O2 | 20.0% |
| 1O1-HH-3 | 6.0% |
| 1O1-HH-5 | 5.0% |
| 3-HH-EMe | 12.0% |
| 4-HEB-O1 | 9.0% |
| 4-HEB-O2 | 7.0% |
| 5-HEB-O1 | 8.0% |
| 3-HHB-1 | 6.0% |
| 3-HHB-3 | 6.0% |
| 4-HEB(2CN,3CN)-O4 | 3.0% |
| 2-HBEB(2CN,3CN)-O2 | 2.0% |
| 4-HBEB(2CN,3CN)-O4 | 4.0% |

$T_{NI} = 69.4$ (° C.)

$\eta$ = 31.5 (mPa · s)
$\Delta n$ = 0.087
$\Delta\epsilon$ = −5.0

Use Example 11

| | |
|---|---|
| 3-HB(F)B(2F,3F)-O2 | 6.0% |
| 1V2-BEB(F,F)-C | 5.0% |
| 3-HB-C | 20.0% |
| V2-HB-C | 6.0% |
| 1-BTB-3 | 5.0% |
| 2-BTB-1 | 10.0% |
| 1O1-HH-3 | 3.0% |
| 3-HH-4 | 11.0% |
| 3-HHB-1 | 5.0% |
| 3-HHB-3 | 3.0% |
| 3-H2BTB-2 | 4.0% |
| 3-H2BTB-3 | 4.0% |
| 3-H2BTB-4 | 4.0% |
| 3-HB(F)TB-2 | 6.0% |
| 3-HB(F)TB-3 | 5.0% |
| 3-HHB-C | 3.0% |

$T_{NI}$ = 85.9 (° C.)
$\eta$ = 17.3 (mPa · s)
$\Delta n$ = 0.164
$\Delta\epsilon$ = 7.2
Vth = 2.07 (V)

Pitch (P) of the twist of the liquid crystal composition obtained by adding 0.8 part by weight of optically active compound CM33 to 100 parts by weight of the composition described above was 11.5 $\mu$m.

| | |
|---|---|
| 3-HB(2F)B(2F,3F)-O2 | 5.0% |
| 3-H2B(2F)B(2F,3F)-O2 | 5.0% |
| V2-HB-TC | 10.0% |
| 3-HB-TC | 10.0% |
| 3-HB-C | 10.0% |
| 5-HB-C | 7.0% |
| 5-BB-C | 3.0% |
| 2-BTB-1 | 10.0% |
| 2-BTB-O1 | 5.0% |
| 3-HH-4 | 5.0% |
| 3-HHB-3 | 11.0% |
| 3-H2BTB-2 | 3.0% |
| 3-H2BTB-3 | 3.0% |
| 3-HB(F)TB-2 | 3.0% |
| 5-BTB(F)TB-3 | 10.0% |

$T_{NI}$ = 94.4 (° C.)
$\eta$ = 15.9 (mPa · s)
$\Delta n$ = 0.209
$\Delta\epsilon$ = 6.8
Vth = 2.18 (V)

Use Example 13

| | |
|---|---|
| 3-HB(F)B(2F,3F)-O2 | 2.0% |
| 3-HB(2F,5F)B(2F,3F)-O2 | 2.0% |
| 1V2-BEB(F,F)-C | 6.0% |
| 3-HB-C | 18.0% |
| 2-BTB-1 | 10.0% |
| 5-HH-VFF | 30.0% |
| 1-BHH-VFF | 8.0% |
| 1-BHH-2VFF | 11.0% |
| 3-H2BTB-2 | 5.0% |
| 3-H2BTB-3 | 4.0% |
| 3-H2BTB-4 | 4.0% |

$T_{NI}$ = 77.8 (° C.)
$\eta$ = 13.7 (mPa · s)
$\Delta n$ = 0.131
$\Delta\epsilon$ = 6.4
Vth = 2.21 (V)

Use Example 14

| | |
|---|---|
| 3-HB(2F)B(2F,3F)-O2 | 2.0% |
| 3-HB-CL | 10.0% |
| 5-HB-CL | 4.0% |
| 7-HB-CL | 4.0% |
| 1O1-HH-5 | 5.0% |
| 2-HBB(F)-F | 8.0% |
| 3-HBB(F)-F | 8.0% |
| 5-HBB(F)-F | 14.0% |
| 4-HHB-CL | 8.0% |
| 5-HHB-CL | 8.0% |
| 3-H2HB(F)-CL | 4.0% |
| 3-HBB(F,F)-F | 10.0% |
| 5-H2BB(F,F)-F | 9.0% |
| 3-HB(F)VB-2 | 2.0% |
| 3-H2BTB-2 | 4.0% |

$T_{NI}$ = 89.9 (° C.)
$\eta$ = 20.5 (mPa · s)
$\Delta n$ = 0.127
$\Delta\epsilon$ = 4.9
Vth = 2.33 (V)

Use Example 15

| | |
|---|---|
| 3-HB(F)B(2F,3F)-O2 | 2.0% |
| 3-HB(2F)B(2F,3F)-O2 | 2.0% |
| 3-H2B(2F)B(2F,3F)-O2 | 2.0% |
| 2-HHB(F)-F | 2.0% |
| 3-HHB(F)-F | 2.0% |
| 5-HHB(F)-F | 2.0% |
| 3-HBB(F)-F | 6.0% |
| 5-HBB(F)-F | 10.0% |
| 2-H2BB(F)-F | 9.0% |
| 3-H2BB(F)-F | 9.0% |
| 3-HBB(F,F)-F | 25.0% |
| 5-HBB(F,F)-F | 19.0% |
| 1O1-HBBH-4 | 5.0% |
| 1O1-HBBH-5 | 5.0% |

$T_{NI}$ = 98.3 (° C.)
$\eta$ = 36.5 (mPa · s)
$\Delta n$ = 0.137
$\Delta\epsilon$ = 7.0
Vth = 2.13 (V)

Pitch (P) of the twist of the liquid crystal composition obtained by adding 0.2 part by weight of optically active compound CM43L to 100 parts by weight of the composition described above was 77.8 $\mu$m.

| | |
|---|---|
| 3-HB(F)B(2F,3F)-O2 | 15.0% |
| 5-HB(F)B(2F,3F)-O2 | 10.0% |
| 3-HB(2F)B(2F,3F)-O2 | 15.0% |
| 5-HB(2F)B(2F,3F)-O2 | 10.0% |
| 3-HHB(2F,3F)-O2 | 10.0% |
| 5-HHB(2F,3F)-O2 | 10.0% |
| 3-HB-O2 | 20.0% |
| 3-HH-4 | 10.0% |

$T_{NI}$ = 109.1 (° C.)
$\Delta n$ = 0.130
$\Delta\epsilon$ = −4.5

Liquid crystalline compounds of the present invention have a negative and extremely large dielectric anisotropy value and a small optical anisotropy value at the same time. Also, the compounds exhibit an excellent characteristic even in the miscibility with other liquid crystal materials. Accordingly, liquid crystal compositions exhibiting both a low threshold voltage and a small optical anisotropy value can be actualized by using the liquid crystalline compound of the present invention as component of liquid crystal compositions. Further, it is possible to provide excellent liquid crystal display devices by using the liquid crystal composition.

Typical compound of the present invention (compound of Example 1) exhibits 25% larger dielectric anisotropy value than the compound (compound of Comparative Example 1) reported by V. Reiffenrath et al. (Liq. Cryst., 5 (1), 159 (1989)). On the other hand, whereas the compound of Comparative Example 1 is 0.188 in optical anisotropy value, the compound of Example 1 is as small as 0.155 and preferable as component of liquid crystal compositions for IPS mode and VA mode.

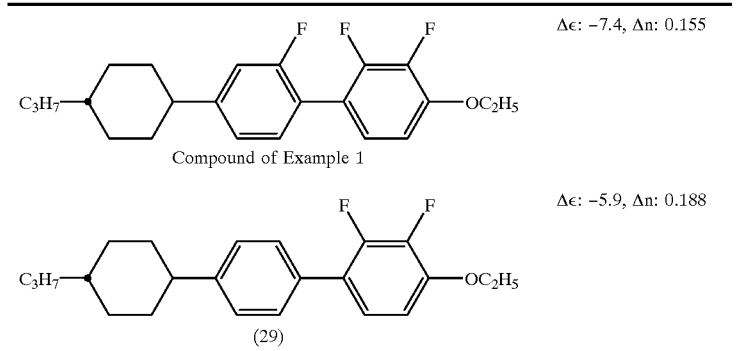

Also, whereas hitherto known terphenyl compounds, for example, compound (14), has an extremely narrow temperature range of nematic phase and a wide smectic phase range, the compound of Example 1 exhibited a wide temperature range of nematic phase and an excellent miscibility.

Excellent characteristics of the liquid crystalline compounds of the present invention described above contradict to the existing concept (theory of Maier and Meier) described above. Liquid crystalline compounds having such excellent characteristics have not been known at all up to now.

INDUSTRIAL APPLICABILITY

Liquid crystalline compounds of the present invention can preferably be employed as component of liquid crystal compositions not only for IPS mode and VA mode but also for ECB (electrically controlled birefringence) mode and GH (guest-host) mode. Also, the compounds can preferably be employed as component of liquid crystal compositions for TN (twisted nematic), STN (super twisted nematic), and AM (active matrix) modes.

What is claimed is:

1. A liquid crystalline compound expressed by the general formula (1)

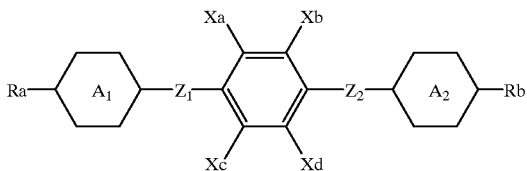

wherein Ra and Rb each independently represent a straight chain or branched alkyl group or alkoxy group having 1 to 10 carbon atoms, or a straight or branched alkenyl group or alkynyl group having 2 to 10 carbon atoms; ring $A_1$ represents cyclohexane-1,4-diyl in which ring not-adjacent any methylene group may be replaced by —O—; ring $A_2$ represents 2,3-difluoro-1,4-phenylene in which phenylene hydrogen atoms at 5-position and 6-position may each independently be replaced by fluorine atoms but there is not a case wherein both of the hydrogen atoms are simultaneously replaced; $Z_1$ and $Z_2$ each independently represent single bond or —CH$_2$CH$_2$—; Xa, Xb, Xc, and Xd each independently represent hydrogen atom, fluorine atom, or chlorine atom, but at least one of Xa, Xb, Xc, and Xd is fluorine atom or chlorine atom; and any atom which constitutes the compound may be replaced by its isotope.

2. The liquid crystalline compound according to claim 1 wherein both $Z_1$ and $Z_2$ are single bonds, ring $A_2$ is 2,3-difluoro-1,4-phenylene, Xa is fluorine atom, and all of Xb, Xc, and Xd are hydrogen atoms.

3. The liquid crystalline compound according to claim 1 wherein both $Z_1$ and $Z_2$ are single bonds, ring $A_2$ is 2,3-difluoro-1,4-phenylene, Xb is fluorine atom, and all of Xa, Xc, and Xd are hydrogen atoms.

4. The liquid crystalline compound according to claim 1 wherein both $Z_1$ and $Z_2$ are single bonds, ring $A_2$ is 2,3-difluoro-1,4-phenylene, both Xa and Xd are fluorine atoms, and both Xb and Xc are hydrogen atoms.

5. The liquid crystalline compound according to claim 1 wherein both $Z_1$ and $Z_2$ are single bonds, ring $A_2$ is 2,3-difluoro-1,4-phenylene, both Xa and Xb are fluorine atoms, and both Xc and Xd are hydrogen atoms.

6. The liquid crystalline compound according to claim 1 wherein $Z_1$ is —CH$_2$CH$_2$—, $Z_2$ is single bond, ring $A_2$ is 2,3-difluoro-1,4-phenylene, Xa is fluorine atom, and all of Xb, Xc, and Xd are hydrogen atoms.

7. The liquid crystalline compound according to claim 1 wherein $Z_1$ is —CH$_2$CH$_2$—, $Z_2$ is single bond, ring $A_2$ is 2,3-difluoro-1,4-phenylene, Xb is fluorine atom, and all of Xa, Xc, and Xd are hydrogen atoms.

8. The liquid crystalline compound according to claim 1 wherein $Z_1$ is —CH$_2$CH$_2$—, $Z_2$ is single bond, ring $A_2$ is 2,3-difluoro-1,4-phenylene, both Xa and Xd are fluorine atoms, and both Xb and Xc are hydrogen atoms.

9. The liquid crystalline compound according to claim 1 wherein $Z_1$ is —CH$_2$CH$_2$—, $Z_2$ is single bond, ring $A_2$ is 2,3-difluoro-1,4-phenylene, both Xa and Xb are fluorine atoms, and both Xc and Xd are hydrogen atoms.

10. A liquid crystal composition comprising at least one liquid crystalline compound defined in claim 1.

11. A liquid crystal composition comprising, as a first component, at least one liquid crystalline compound defined in claim 1 and comprising, as a second component, at least one compound selected from the group consisting of the compounds expressed by any one of the general formulas (2), (3), and (4)

(2)

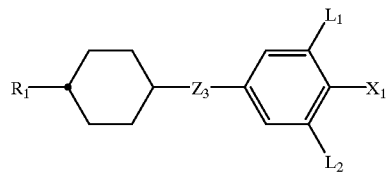

(3)

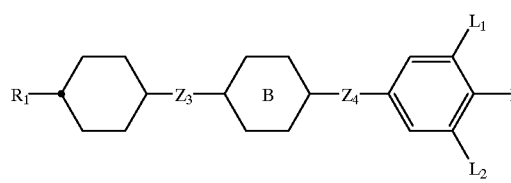

(4)

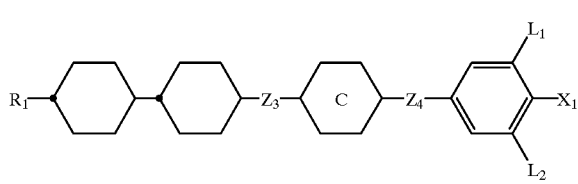

wherein $R_1$ represents an alkyl group having 1 to 10 carbon atoms in which group not-adjacent any methylene group may be replaced by —O— or —CH=CH— and any hydrogen atom in the group may be replaced by fluorine atom; $X_1$ represents fluorine atom, chlorine atom, —OCF$_3$, —OCF$_2$H, —CF$_3$, —CF$_2$H, —CFH$_2$, —OCF$_2$CF$_2$H, or —OCF$_2$CFHCF$_3$; $L_1$ and $L_2$ each independently represent hydrogen atom or fluorine atom; $Z_3$ and $Z_4$ each independently represent —CH$_2$CH$_2$—, —(CH$_2$)$_4$—, —COO—, —CF$_2$O—, —OCF$_2$—, —CH=CH—, or single bond; ring B represents cyclohexane-1,4-diyl or 1,3-dioxane-2,5-diyl, or 1,4-phenylene in which hydrogen atom may be replaced by fluorine atom; ring C represents cyclohexane-1,4-diyl, or 1,4-phenylene in which hydrogen atom may be replaced by fluorine atom; and any atom which constitutes these compounds may be replaced by its isotope.

12. A liquid crystal composition comprising, as a first component, at least one liquid crystalline compound defined in claim 1 and comprising, as a second component, at least one compound selected from the group consisting of the compounds expressed by any one of the general formulas (5) or (6)

(5)

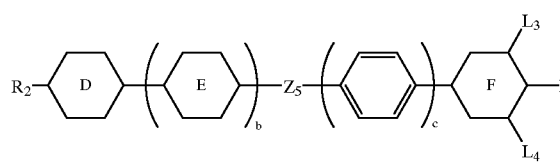

(6)

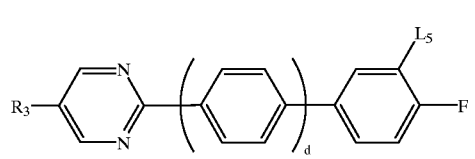

wherein $R_2$ and $R_3$ each independently represent an alkyl group having 1 to 10 carbon atoms in which group not-adjacent any methylene group may be replaced by —O— or —CH=CH— and any hydrogen atom in the group may be replaced by fluorine atom; $X_2$ represents —CN or —C≡C—CN; ring D represents cyclohexane-1,4-diyl, 1,4-phenylene, 1,3-dioxane-2,5-diyl, or pyrimidine-2,5-diyl; ring E represents cyclohexane-1,4-diyl, 1,4-phenylene in which hydrogen atom may be replaced by fluorine atom, or pyrimidine-2,5-diyl; ring F represents cyclohexane-1,4-diyl or 1,4-phenylene; $Z_5$ represents —CH$_2$CH$_2$—, —COO—, or single bond; $L_3$, $L_4$, and $L_5$ each independently represent hydrogen atom or fluorine atom; b, c, and d are each independently 0 or 1; and any atom which constitutes these compounds may be replaced by its isotope.

13. A liquid crystal composition comprising, as a first component, at least one liquid crystalline compound defined in claim 1 and comprising, as a second component, at least one compound selected from the group consisting of the compounds expressed by any one of the general formulas (7), (8), and (9)

(7)

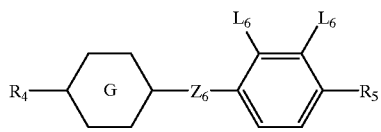

(8)

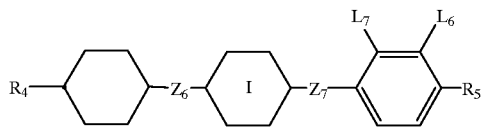

(9)

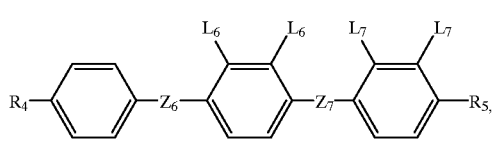

wherein $R_4$ and $R_5$ each independently represent an alkyl group having 1 to 10 carbon atoms in which group not-adjacent any methylene group may be replaced by —O— or —CH=CH— and any hydrogen atom in the group may be replaced by fluorine atom; ring G and ring I each independently represent cyclohexane-1,4-diyl or 1,4-phenylene; $L_6$ and $L_7$ each independently represent hydrogen atom, cyano group, or fluorine atom, but there is not a case wherein $L_6$ and $L_7$ represent hydrogen atom at the same time; $Z_6$ and $Z_7$ each independently represent —CH$_2$CH$_2$—, —COO—, or single bond; and any atom which constitutes these compounds may be replaced by its isotope.

14. A liquid crystal composition comprising, as a first component, at least one liquid crystalline compound defined in claim 1, comprising, as a second component, at least one compound selected from the group consisting of the compounds expressed by any one of the general formulas (2), (3), and (4), and comprising, as a third component, at least one compound selected from the group consisting of the compounds expressed by any one of the general formulas (10), (11), and (12)

(2)

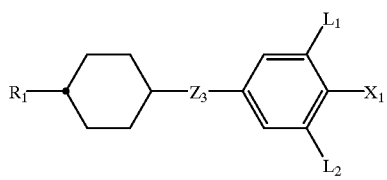

(3)

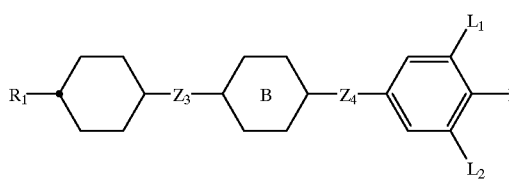

(4)

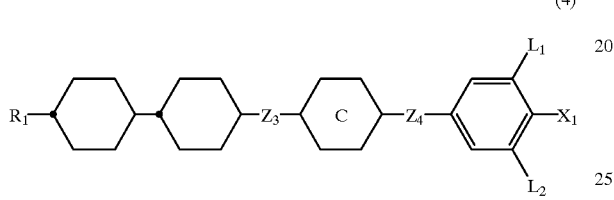

wherein R₁ represents an alkyl group having 1 to 10 carbon atoms in which group not-adjacent any methylene group may be replaced by —O— or —CH=CH— and any hydrogen atom in the group may be replaced by fluorine atom; X₁ represents fluorine atom, chlorine atom, —OCF₃, —OCF₂H, —CF₃, —CF₂H, —CFH₂, —OCF₂CF₂H, or —OCF₂CFHCF₃; L₁ and L₂ each independently represent hydrogen atom or fluorine atom; Z₃ and Z₄ each independently represent —CH₂CH₂—, —(CH₂)₄—, —COO—, —CF₂O—, —OCF₂—, —CH=CH—, or single bond; ring B represents cyclohexane-1,4-diyl or 1,3-dioxane-2,5-diyl, or 1,4-phenylene in which hydrogen atom may be replaced by fluorine atom; ring C represents cyclohexane-1,4-diyl, or 1,4-phenylene in which hydrogen atom may be replaced by fluorine atom; and any atom which constitutes these compounds may be replaced by its isotope, (10)

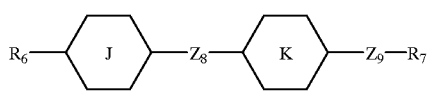

(11)

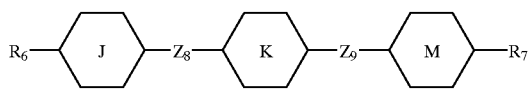

(12)

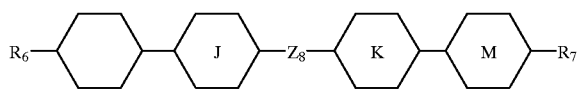

wherein R₆ and R₇ each independently represent an alkyl group having 1 to 10 carbon atoms in which group not-adjacent any methylene group may be replaced by —O— or —CH=CH— and any hydrogen atom in the group may be replaced by fluorine atom; ring J, ring K, and ring M each independently represent cyclohexane-1,4-diyl or pyrimidine-2,5-diyl, or 1,4-phenylene in which hydrogen atom may be replaced by fluorine atom; Z₈ and Z₉ each independently represent —CH₂CH₂—, —C—C—, —COO—, —CH=CH—, or single bond; and any atom which constitutes these compounds may be replaced by its isotope.

15. A liquid crystal composition comprising, as a first component, at least one liquid crystalline compound defined in claim 1, comprising, as a second component, at least one compound selected from the group consisting of the compounds expressed by the general formula (5) or (6), and comprising, as a third component, at least one compound selected from the group consisting of the compounds expressed by any one of the general formulas (10), (11), and (12)

(5)

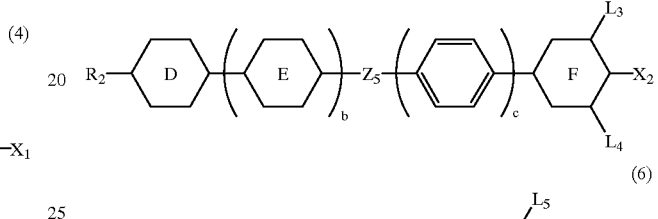

(6)

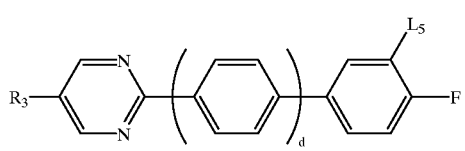

wherein R₂ and R₃ each independently represent an alkyl group having 1 to 10 carbon atoms in which group not-adjacent any methylene group may be replaced by —O— or —CH=CH— and any hydrogen atom in the group may be replaced by fluorine atom; X₂ represents —CN or —C≡C—CN; ring D represents cyclohexane-1,4-diyl, 1,4-phenylene, 1,3-dioxane-2,5-diyl, or pyrimidine-2,5-diyl; ring E represents cyclohexane-1,4-diyl, 1,4-phenylene in which hydrogen atom may be replaced by fluorine atom, or pyrimidine-2,5-diyl; ring F represents cyclohexane-1,4-diyl or 1,4-phenylene; Z₅ represents —CH₂CH₂—, —COO—, or single bond; L₃, L₄, and L₅ each independently represent hydrogen atom or fluorine atom; b, c, and d are each independently 0 or 1; and any atom which constitutes these compounds may be replaced by its isotope, (10)

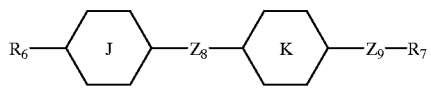

(11)

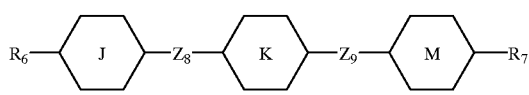

(12)

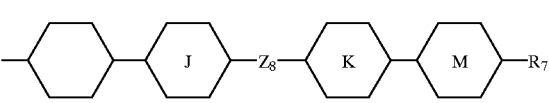

wherein R₆ and R₇ each independently represent an alkyl group having 1 to 10 carbon atoms in which group not-adjacent any methylene group may be replaced by —O— or —CH=CH— and any hydrogen atom in the group may be replaced by fluorine atom; ring J, ring K, and ring M each independently represent cyclohexane-1,4-diyl or pyrimidine-2,5-diyl, or 1,4-phenylene in which hydrogen atom may be replaced by fluorine atom; $Z_8$ and $Z_9$ each independently represent —$CH_2CH_2$—, —C≡C—, —COO—, —CH=CH—, or single bond; and any atom which constitutes these compounds may be replaced by its isotope.

16. A liquid crystal composition comprising, as a first component, at least one liquid crystalline compound defined in claim 1, comprising, as a second component, at least one compound selected from the group consisting of the compounds expressed by any one of the general formulas (7), (8), and (9), and comprising, as a third component, at least one compound selected from the group consisting of the compounds expressed by any one of the general formulas (10), (11), and (12)

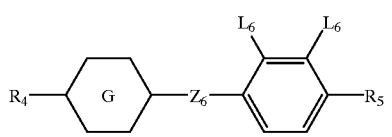

(7)

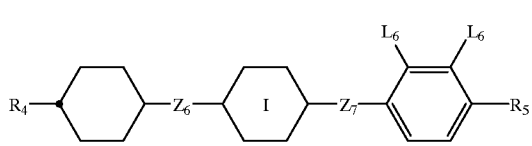

(8)

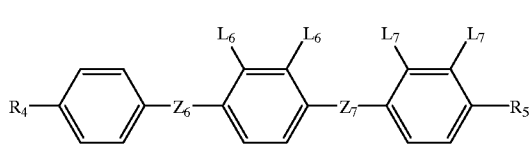

(9)

wherein $R_4$ and $R_5$ each independently represent an alkyl group having 1 to 10 carbon atoms in which group not-adjacent any methylene group may be replaced by —O— or —CH=CH— and any hydrogen atom in the group may be replaced by fluorine atom; ring G and ring I each independently represent cyclohexane-1,4-diyl or 1,4-phenylene; $L_6$ and $L_7$ each independently represent hydrogen atom, cyano group, or fluorine atom, but there is not a case wherein $L_6$ and $L_7$ represent hydrogen atom at the same time; $Z_6$ and $Z_7$ each independently represent —$CH_2CH_2$—, —COO—, or single bond; and any atom which constitutes these compounds may be replaced by its isotope,

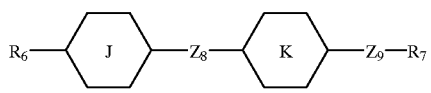

(10)

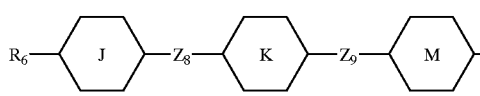

(11)

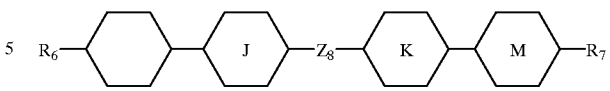

(12)

wherein $R_6$ and $R_7$ each independently represent an alkyl group having 1 to 10 carbon atoms in which group not-adjacent any methylene group may be replaced by —O— or —CH=CH— and any hydrogen atom in the group may be replaced by fluorine atom; ring J, ring K, and ring M each independently represent cyclohexane-1,4-diyl or pyrimidine-2,5-diyl, or 1,4-phenylene in which hydrogen atom may be replaced by fluorine atom; $Z_8$ and $Z_9$ each independently represent —$CH_2CH_2$—, —C≡C—, —COO—, —CH=CH—, or single bond; and any atom which constitutes these compounds may be replaced by its isotope.

17. A liquid crystal composition comprising, as a first component, at least one liquid crystalline compound defined in claim 1, comprising, as a second component, at least one compound selected from the group consisting of the compounds expressed by any one of the general formulas (2), (3), and (4), comprising, as a third component, at least one compound selected from the group consisting of the compounds expressed by the general formula (5) or (6), and comprising, as a fourth component, at least one compound selected from the group consisting of the compounds expressed by any one of the general formulas (10), (11), and (12)

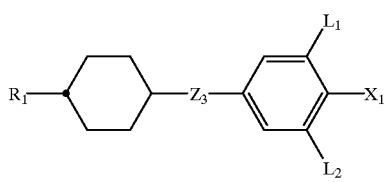

(2)

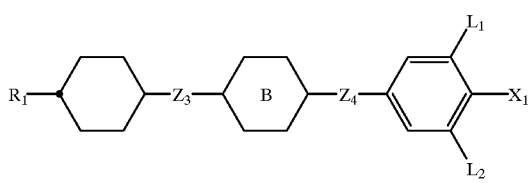

(3)

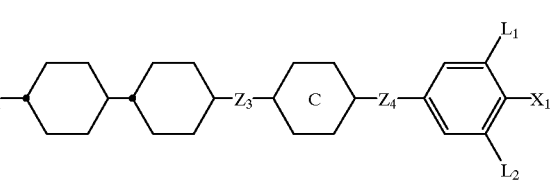

(4)

wherein $R_1$ represents an alkyl group having 1 to 10 carbon atoms in which group not-adjacent any methylene group may be replaced by —O— or —CH=CH— and any hydrogen atom in the group may be replaced by fluorine atom; $X_1$ represents fluorine atom, chlorine atom, —$OCF_3$, —$OCF_2H$, —$CF_3$, —$CF_2H$, —$CFH_2$, —$OCF_2CF_2H$, or —$OCF_2CFHCF_3$; $L_1$ and $L_2$ each independently represent hydrogen atom or fluorine atom; $Z_3$ and $Z_4$ each independently represent —$CH_2CH_2$—, —$(CH_2)_4$—, —COO—, —CF$_2$O—, —OCF$_2$—, —CH=CH—, or single bond; ring B represents cyclohexane-1,4-diyl or 1,3-dioxane-2,5-diyl, or 1,4-phenylene in which hydrogen atom may be replaced by fluorine atom; ring C represents cyclohexane-1,4-diyl, or 1,4-phenylene in which hydrogen atom may be replaced by fluorine atom; and any atom which constitutes these compounds may be replaced by its isotope,

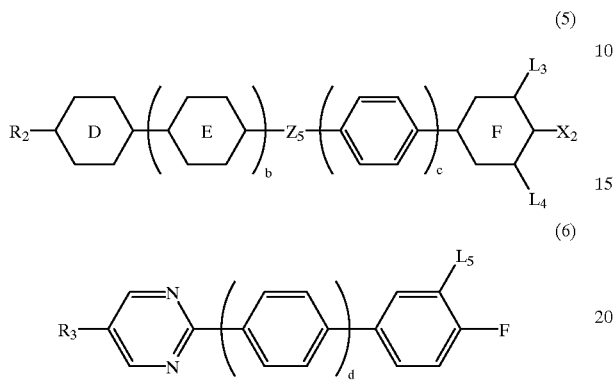

wherein R$_2$ and R$_3$ each independently represent an alkyl group having 1 to 10 carbon atoms in which group not-adjacent any methylene group may be replaced by —O— or —CH=CH— and any hydrogen atom in the group may be replaced by fluorine atom; X$_2$ represents —CN or —C≡C—CN; ring D represents cyclohexane-1,4-diyl, 1,4-phenylene, 1,3-dioxane-2,5-diyl, or pyrimidine-2,5-diyl; ring E represents cyclohexane-1,4-diyl, 1,4-phenylene in which hydrogen atom may be replaced by fluorine atom, or pyrimidine-2,5-diyl; ring F represents cyclohexane-1,4-diyl or 1,4-phenylene; Z$_5$ represents —CH$_2$CH$_2$—, —COO—, or single bond; L$_3$, L$_4$, and L$_5$ each independently represent hydrogen atom or fluorine atom; b, c, and d are each independently 0 or 1; and any atom which constitutes these compounds may be replaced by its isotope,

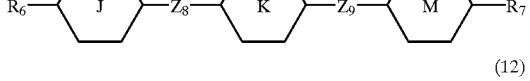

wherein R$_6$ and R$_7$ each independently represent an alkyl group having 1 to 10 carbon atoms in which group not-adjacent any methylene group may be replaced by —O— or —CH=CH— and any hydrogen atom in the group may be replaced by fluorine atom; ring J, ring K, and ring M each independently represent cyclohexane-1,4-diyl or pyrimidine-2,5-diyl, or 1,4-phenylene in which hydrogen atom may be replaced by fluorine atom; Z$_8$ and Z$_9$ each independently represent —CH$_2$CH$_2$—, —C≡C—, —COO—, —CH=CH—, or single bond; and any atom which constitutes these compounds may be replaced by its isotope.

18. A liquid crystal composition defined in any one of claims 10 to 13 or 14–17, further comprising one or more optically active compounds.

19. A liquid crystal display device comprising a liquid crystal composition defined in claim 10.

* * * * *

UNITED STATES PATENT AND TRADEMARK OFFICE
CERTIFICATE OF CORRECTION

PATENT NO.   : 6,348,244 B1  Page 1 of 1
DATED        : February 19, 2002
INVENTOR(S)  : Kazutoshi Miyazawa et al.

It is certified that error appears in the above-identified patent and that said Letters Patent is hereby corrected as shown below:

Column 10,
Line 49, delete "13"
Line 52, change "1,4,-phenylehe" to -- 1,4-phenylene --

Column 36,
Line 62, change "xb" to -- Xb --

Column 66,
Line 31, (general formula (8), change "$L_7$" to -- $L_6$ --

Column 68,
Line 2, change "-C-C-" to -- -C $\equiv$ C- --.

Signed and Sealed this

Twenty-fourth Day of September, 2002

Attest:

Attesting Officer

JAMES E. ROGAN
*Director of the United States Patent and Trademark Office*